(12) United States Patent
Li et al.

(10) Patent No.: US 9,738,691 B2
(45) Date of Patent: Aug. 22, 2017

(54) TRUNCATED L1 PROTEIN OF HUMAN PAPILLOMAVIRUS TYPE 58

(71) Applicants: XIAMEN UNIVERSITY, Xiamen (CN); XIAMEN INNOVAX BIOTECH CO., LTD., Xiamen (CN)

(72) Inventors: Shaowei Li, Xiamen (CN); Minxi Wei, Xiamen (CN); Xianglin Kong, Xiamen (CN); Yingbin Wang, Xiamen (CN); Jun Zhang, Xiamen (CN); Ningshao Xia, Xiamen (CN)

(73) Assignees: XIAMEN UNIVERSITY, Fujian Province (CN); XIAMEN INNOVAX BIOTECH CO., LTD., Fujian (CN)

( * ) Notice: Subject to any disclaimer, the term of this patent is extended or adjusted under 35 U.S.C. 154(b) by 0 days.

(21) Appl. No.: 15/057,416

(22) Filed: Mar. 1, 2016

(65) Prior Publication Data

US 2016/0200776 A1    Jul. 14, 2016

Related U.S. Application Data

(62) Division of application No. 13/810,581, filed as application No. PCT/CN2011/077184 on Jul. 15, 2011.

(30) Foreign Application Priority Data

Jul. 16, 2010 (CN) .......................... 2010 1 0232875

(51) Int. Cl.
| | |
|---|---|
| *A61K 39/12* | (2006.01) |
| *C07K 14/005* | (2006.01) |
| *C12N 7/00* | (2006.01) |
| *A61K 39/00* | (2006.01) |
| *A61K 38/00* | (2006.01) |

(52) U.S. Cl.
CPC ............ *C07K 14/005* (2013.01); *A61K 39/12* (2013.01); *C12N 7/00* (2013.01); *A61K 38/00* (2013.01); *A61K 2039/5258* (2013.01); *A61K 2039/585* (2013.01); *C12N 2710/20022* (2013.01); *C12N 2710/20023* (2013.01); *C12N 2710/20034* (2013.01)

(58) Field of Classification Search
None
See application file for complete search history.

(56) References Cited

U.S. PATENT DOCUMENTS

2003/0118609 A1    6/2003  Harrison et al.
2007/0036824 A1*   2/2007  Bryan ..................... C12N 7/00
                                                      424/204.1

FOREIGN PATENT DOCUMENTS

| CN | 101518647 | 9/2009 |
| CN | 101857870 A | 10/2010 |
| WO | 2005047315 A2 | 5/2005 |

OTHER PUBLICATIONS

Machine English translation of CN 101153280 A.*
Kozak. Point Mutations Define a Sequence Flanking the AUG Initiator Codon That Modulates Translation by Eukaryotic Ribosomes. Cell, vol. 44, 283-292, Jan. 31, 1986.*
Zemskovaa et al. Transient expression of deletion mutants of the herpes simplex virus thymidine kinase-encoding gene in mouse fibroblast cells. Gene. vol. 106, Issue 2, Oct. 15.*
Banks et al., "Expression of human papillomavirus type 6 and type 16 capsid proteins in bacteria and their antigenic characterization," J. Gen. Virol. 68, 3081-89, 1987.
Bao et al., "Human papillomavirus type-distribution in the cervix of Chinese women: a meta-analysis," Int. J. STD & AIDS 19, 106-11, 2007.
Boyle & Ferlay, "Cancer incidence and mortality in Europe," Ann. Oncol. 16, 481-88, 2005.
Brummell et al., "Probing the combining site of an anti-carbohydrate antibody by saturation-mutagenesis role of the heavy-chain CDR3 residues," Biochem. 32, 1180-87, 1993.
Burks et al., "In vitro scanning saturation mutagenesis of an antibody binding pocket," Proc. Nat'l. Acad. Sci. USA 94, 412-17, 1997.
Chen et al., "Papillomavirus Capsid Protein Expression in *Escherichia coli*: Purification and Assembly of HPV11 and HPV16 L1," J. Mol. Biol., 2001, vol. 307, pp. 173-182.
Clifford et al., "Human papillomavirus types in invasive cervical cancer worldwide: a meta analysis," Br. J. Cancer 88, 63-73, 2003.
Database Nucleotide [Online] Dec. 7, 2007, "Human Papillomavirus Type 58 Complete Genome," XP002715984, retrieved from NCBI Database accession No. D90400.1.
Database UniParc [Online], Database Accession No. UPI0001A4DFE6, May 25, 2009, XP002715983 (http://www.uniprot.org/uniparc/UPI0001A4DFE6, Jun. 11, 2013).
Extended European Search Report for EP Application No. 11806304.9, dated Dec. 11, 2013.
Fey et al., "Demonstration of in Vitro Synthesis of Human Papilloma Viral Proteins from Hand and Foot Warts," J. Invest. Dermatol., Jun. 1989, vol. 92, No. 6, pp. 817-824.
Fu et al., "New human papilioma virus (HPV)58L1 gene, useful for biological applications," Database WPI, XP002715985.
International Search Report for PCT/CN2011/077184 mailed Oct. 27, 2011.
Kelsall & Kulski "Expression of the major capsid protein of human papillomavirus type 16 in *Eschericia coli*," J. Virol. Meth. 53, 75-90, 1995.
Kirii et al., "Human Papillomavirus Type 58 Complete Genome," Virology, 1991, vol. 185, No. 1, pp. 424-427, Database Nucleotide [Online], Dec. 7, 2007, Database Accession No. D90400.1, XP002715984.

(Continued)

*Primary Examiner* — Nianxiang (Nick) Zou
(74) *Attorney, Agent, or Firm* — Banner & Witcoff, Ltd.

(57) ABSTRACT

Provided are an N-terminal truncated L1 protein of the Human Papillomavirus Type 58, a coding sequence and preparation method thereof, and a virus-like particle comprising the protein. Uses of the protein and the virus-like particle in the preparation of a pharmaceutical composition or a vaccine are further provided. The pharmaceutical composition or vaccine is used for prevention of HPV infection and a disease caused by HPV infection.

10 Claims, 15 Drawing Sheets

(56) References Cited

OTHER PUBLICATIONS

Kirnbauer et al., "Papillomavirus Li major capsid protein self-assembles into virus-like particles that are highly immunogenic," Proc. Nat'l. Acad. Sci. USA 89, 12188-84, 1992.

Kobayashi et al., "Tryptophan H33 plays an important role in pyrimidine (6-4) pyrimidone photoproduct binding by a high-affinity antibody," Prot. Eng. 12, 879-84, 1999.

Kozak, "Point Mutations Define a Sequence Flanking the AUG Initiator Codon That Modulates Translation by Eukaryotic Robosomes," Cell, vol. 44, 283-292, Jan. 31, 1986.

Li et al., "Carboxyl Terminus Truncated HPV58 Virus L1 Protein Expressed with Baculovirus System and its Bioactivity," Chinese Journal of Biotechnology, Jul. 2004, vol. 20, No. 4, pp. 536-539.

Li et al., "Expression of the Human Papillomavirus Type 11 L1 Capsid Protein in *Escherichia coli* Characterization of Protein Domains Involved in DNA Binding and Capsid Assembly," J. Virol. 71, 2988095, 1997.

Myers & Miller, "Optimal alignments in linear space," Comput. Appl. Biosci. 4, 11-17, 1988.

Needleman & Wunsch, "A general method applicable to the search for similarities in the amino acid sequence of two proteins," J. Mol. Biol. 48, 445-53, 1970.

Wang et al., "Translational comparison of HPV58 long and short L1 mRNAs in yeast (*Saccharomyces cerevisiae*) cell-free system," Journal of Bioscience and Bioengineering, 2010, vol. 110, No. 1, pp. 58-65.

Zemskovaa et al., "Transient Expression of Deletion Mutants of the Herpes Simplex Virus Thymidine Kinase-Encoding Gene in Mouse Fibroflast Cells," Gene, vol. 106, Issue 2, Oct. 15.

\* cited by examiner

SEQUENCE LISTING

```
<160> NUMBER OF SEQ ID NOS: 17

<210> SEQ ID NO 1
<211> LENGTH: 490
<212> TYPE: PRT
<213> ORGANISM: Artificial sequence
<220> FEATURE:
<223> OTHER INFORMATION: Truncated HPV58 L1 protein

<400> SEQUENCE: 1

Met Thr Val Tyr Leu Pro Pro Val Pro Val Ser Lys Val Val Ser Thr
1               5                   10                  15

Asp Glu Tyr Val Ser Arg Thr Ser Ile Tyr Tyr Ala Gly Ser Ser
            20                  25                  30

Arg Leu Leu Ala Val Gly Asn Pro Tyr Phe Ser Ile Lys Ser Pro Asn
        35                  40                  45

Asn Asn Lys Lys Val Leu Val Pro Lys Val Ser Gly Leu Gln Tyr Arg
    50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Val Ser Gly
            100                 105                 110

His Pro Tyr Leu Asn Lys Phe Asp Asp Thr Glu Thr Ser Asn Arg Tyr
        115                 120                 125

Pro Ala Gln Pro Gly Ser Asp Asn Arg Glu Cys Leu Ser Met Asp Tyr
    130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Ala Ala Ala Thr Asp
                165                 170                 175
```

```
Cys Pro Pro Leu Glu Leu Phe Asn Ser Ile Ile Glu Asp Gly Asp Met
            180                 185                 190

Val Asp Thr Gly Phe Gly Cys Met Asp Phe Gly Thr Leu Gln Ala Asn
        195                 200                 205

Lys Ser Asp Val Pro Ile Asp Ile Cys Asn Ser Thr Cys Lys Tyr Pro
    210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Asn Arg Ala
            245                 250                 255

Gly Lys Leu Gly Glu Ala Val Pro Asp Asp Leu Tyr Ile Lys Gly Ser
            260                 265                 270

Gly Asn Thr Ala Val Ile Gln Ser Ser Ala Phe Phe Pro Thr Pro Ser
            275                 280                 285

Gly Ser Ile Val Thr Ser Glu Ser Gln Leu Phe Asn Lys Pro Tyr Trp
            290                 295                 300

Leu Gln Arg Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
            325                 330                 335

Cys Thr Glu Val Thr Lys Glu Gly Thr Tyr Lys Asn Asp Asn Phe Lys
            340                 345                 350

Glu Tyr Val Arg His Val Glu Glu Tyr Asp Leu Gln Phe Val Phe Gln
            355                 360                 365

Leu Cys Lys Ile Thr Leu Thr Ala Glu Ile Met Thr Tyr Ile His Thr
370                 375                 380

Met Asp Ser Asn Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
            405                 410                 415

Ile Thr Cys Gln Lys Thr Ala Pro Pro Lys Glu Lys Glu Asp Pro Leu
            420                 425                 430

Asn Lys Tyr Thr Phe Trp Glu Val Asn Leu Lys Glu Lys Phe Ser Ala
            435                 440                 445

Asp Leu Asp Gln Phe Pro Leu Gly Arg Lys Phe Leu Leu Gln Ser Gly
450                 455                 460

Leu Lys Ala Lys Pro Arg Leu Lys Arg Ser Ala Pro Thr Thr Arg Ala
465                 470                 475                 480

Pro Ser Thr Lys Arg Lys Lys Val Lys Lys
            485                 490

<210> SEQ ID NO 2
<211> LENGTH: 520
<212> TYPE: PRT
<213> ORGANISM: Artificial sequence
<220> FEATURE:
<223> OTHER INFORMATION: Truncated HPV58 L1 protein

<400> SEQUENCE: 2

Met Cys Cys Thr Leu Ala Ile Leu Phe Cys Val Ala Asp Val Asn Val
1               5                   10                  15

Phe His Ile Phe Leu Gln Met Ser Val Trp Arg Pro Ser Glu Ala Thr
            20                  25                  30

Val Tyr Leu Pro Pro Val Pro Val Ser Lys Val Val Ser Thr Asp Glu
            35                  40                  45
```

-continued

```
Tyr Val Ser Arg Thr Ser Ile Tyr Tyr Ala Gly Ser Ser Arg Leu
     50              55                  60

Leu Ala Val Gly Asn Pro Tyr Phe Ser Ile Lys Ser Pro Asn Asn
 65              70                  75                  80

Lys Lys Val Leu Val Pro Lys Val Ser Gly Leu Gln Tyr Arg Val Phe
                 85                  90                  95

Arg Val Arg Leu Pro Asp Pro Asn Lys Phe Gly Phe Pro Asp Thr Ser
            100                 105                 110

Phe Tyr Asn Pro Asp Thr Gln Arg Leu Val Trp Ala Cys Val Gly Leu
            115                 120                 125

Glu Ile Gly Arg Gly Gln Pro Leu Gly Val Gly Val Ser Gly His Pro
            130                 135                 140

Tyr Leu Asn Lys Phe Asp Asp Thr Glu Thr Ser Asn Arg Tyr Pro Ala
145                 150                 155                 160

Gln Pro Gly Ser Asp Asn Arg Glu Cys Leu Ser Met Asp Tyr Lys Gln
                165                 170                 175

Thr Gln Leu Cys Leu Ile Gly Cys Lys Pro Pro Thr Gly Glu His Trp
            180                 185                 190

Gly Lys Gly Val Ala Cys Asn Asn Ala Ala Ala Thr Asp Cys Pro
        195                 200                 205

Pro Leu Glu Leu Phe Asn Ser Ile Ile Glu Asp Gly Asp Met Val Asp
            210                 215                 220

Thr Gly Phe Gly Cys Met Asp Phe Gly Thr Leu Gln Ala Asn Lys Ser
225                 230                 235                 240

Asp Val Pro Ile Asp Ile Cys Asn Ser Thr Cys Lys Tyr Pro Asp Tyr
                245                 250                 255

Leu Lys Met Ala Ser Glu Pro Tyr Gly Asp Ser Leu Phe Phe Phe Leu
            260                 265                 270

Arg Arg Glu Gln Met Phe Val Arg His Phe Phe Asn Arg Ala Gly Lys
            275                 280                 285

Leu Gly Glu Ala Val Pro Asp Asp Leu Tyr Ile Lys Gly Ser Gly Asn
            290                 295                 300

Thr Ala Val Ile Gln Ser Ser Ala Phe Phe Pro Thr Pro Ser Gly Ser
305                 310                 315                 320

Ile Val Thr Ser Glu Ser Gln Leu Phe Asn Lys Pro Tyr Trp Leu Gln
                325                 330                 335

Arg Ala Gln Gly His Asn Asn Gly Ile Cys Trp Gly Asn Gln Leu Phe
            340                 345                 350

Val Thr Val Val Asp Thr Thr Arg Ser Thr Asn Met Thr Leu Cys Thr
            355                 360                 365

Glu Val Thr Lys Glu Gly Thr Tyr Lys Asn Asp Asn Phe Lys Glu Tyr
            370                 375                 380

Val Arg His Val Glu Glu Tyr Asp Leu Gln Phe Val Phe Gln Leu Cys
385                 390                 395                 400

Lys Ile Thr Leu Thr Ala Glu Ile Met Thr Tyr Ile His Thr Met Asp
                405                 410                 415

Ser Asn Ile Leu Glu Asp Trp Gln Phe Gly Leu Thr Pro Pro Pro Ser
            420                 425                 430

Ala Ser Leu Gln Asp Thr Tyr Arg Phe Val Thr Ser Gln Ala Ile Thr
            435                 440                 445

Cys Gln Lys Thr Ala Pro Pro Lys Glu Lys Glu Asp Pro Leu Asn Lys
450                 455                 460

Tyr Thr Phe Trp Glu Val Asn Leu Lys Glu Lys Phe Ser Ala Asp Leu
```

```
               465                 470                 475                 480
Asp Gln Phe Pro Leu Gly Arg Lys Phe Leu Leu Gln Ser Gly Leu Lys
                485                 490                 495

Ala Lys Pro Arg Leu Lys Arg Ser Ala Pro Thr Thr Arg Ala Pro Ser
                500                 505                 510

Thr Lys Arg Lys Lys Val Lys Lys
                515                 520

<210> SEQ ID NO 3
<211> LENGTH: 510
<212> TYPE: PRT
<213> ORGANISM: Artificial sequence
<220> FEATURE:
<223> OTHER INFORMATION: Truncated HPV58 L1 protein

<400> SEQUENCE: 3

Met Ala Asp Val Asn Val Phe His Ile Phe Leu Gln Met Ser Val Trp
1               5                   10                  15

Arg Pro Ser Glu Ala Thr Val Tyr Leu Pro Val Pro Val Ser Lys
                20                  25                  30

Val Val Ser Thr Asp Glu Tyr Val Ser Arg Thr Ser Ile Tyr Tyr Tyr
                35                  40                  45

Ala Gly Ser Ser Arg Leu Leu Ala Val Gly Asn Pro Tyr Phe Ser Ile
50                  55                  60

Lys Ser Pro Asn Asn Asn Lys Lys Val Leu Val Pro Lys Val Ser Gly
65                  70                  75                  80

Leu Gln Tyr Arg Val Phe Arg Val Arg Leu Pro Asp Pro Asn Lys Phe
                85                  90                  95

Gly Phe Pro Asp Thr Ser Phe Tyr Asn Pro Asp Thr Gln Arg Leu Val
                100                 105                 110

Trp Ala Cys Val Gly Leu Glu Ile Gly Arg Gly Gln Pro Leu Gly Val
                115                 120                 125

Gly Val Ser Gly His Pro Tyr Leu Asn Lys Phe Asp Asp Thr Glu Thr
                130                 135                 140

Ser Asn Arg Tyr Pro Ala Gln Pro Gly Ser Asp Asn Arg Glu Cys Leu
145                 150                 155                 160

Ser Met Asp Tyr Lys Gln Thr Gln Leu Cys Leu Ile Gly Cys Lys Pro
                165                 170                 175

Pro Thr Gly Glu His Trp Gly Lys Gly Val Ala Cys Asn Asn Asn Ala
                180                 185                 190

Ala Ala Thr Asp Cys Pro Pro Leu Glu Leu Phe Asn Ser Ile Ile Glu
                195                 200                 205

Asp Gly Asp Met Val Asp Thr Gly Phe Gly Cys Met Asp Phe Gly Thr
                210                 215                 220

Leu Gln Ala Asn Lys Ser Asp Val Pro Ile Asp Ile Cys Asn Ser Thr
225                 230                 235                 240

Cys Lys Tyr Pro Asp Tyr Leu Lys Met Ala Ser Glu Pro Tyr Gly Asp
                245                 250                 255

Ser Leu Phe Phe Phe Leu Arg Arg Glu Gln Met Phe Val Arg His Phe
                260                 265                 270

Phe Asn Arg Ala Gly Lys Leu Gly Glu Ala Val Pro Asp Asp Leu Tyr
                275                 280                 285

Ile Lys Gly Ser Gly Asn Thr Ala Val Ile Gln Ser Ser Ala Phe Phe
                290                 295                 300

Pro Thr Pro Ser Gly Ser Ile Val Thr Ser Glu Ser Gln Leu Phe Asn
```

```
              305                 310                 315                 320
Lys Pro Tyr Trp Leu Gln Arg Ala Gln Gly His Asn Asn Gly Ile Cys
                325                 330                 335

Trp Gly Asn Gln Leu Phe Val Thr Val Val Asp Thr Thr Arg Ser Thr
                340                 345                 350

Asn Met Thr Leu Cys Thr Glu Val Thr Lys Glu Gly Thr Tyr Lys Asn
                355                 360                 365

Asp Asn Phe Lys Glu Tyr Val Arg His Val Glu Glu Tyr Asp Leu Gln
370                 375                 380

Phe Val Phe Gln Leu Cys Lys Ile Thr Leu Thr Ala Glu Ile Met Thr
385                 390                 395                 400

Tyr Ile His Thr Met Asp Ser Asn Ile Leu Glu Asp Trp Gln Phe Gly
                405                 410                 415

Leu Thr Pro Pro Pro Ser Ala Ser Leu Gln Asp Thr Tyr Arg Phe Val
                420                 425                 430

Thr Ser Gln Ala Ile Thr Cys Gln Lys Thr Ala Pro Pro Lys Glu Lys
                435                 440                 445

Glu Asp Pro Leu Asn Lys Tyr Thr Phe Trp Glu Val Asn Leu Lys Glu
450                 455                 460

Lys Phe Ser Ala Asp Leu Asp Gln Phe Pro Leu Gly Arg Lys Phe Leu
465                 470                 475                 480

Leu Gln Ser Gly Leu Lys Ala Lys Pro Arg Leu Lys Arg Ser Ala Pro
                485                 490                 495

Thr Thr Arg Ala Pro Ser Thr Lys Arg Lys Lys Val Lys Lys
                500                 505                 510

<210> SEQ ID NO 4
<211> LENGTH: 498
<212> TYPE: PRT
<213> ORGANISM: Artificial sequence
<220> FEATURE:
<223> OTHER INFORMATION: Truncated HPV58 L1 protein

<400> SEQUENCE: 4

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
                20                  25                  30

Ile Tyr Tyr Tyr Ala Gly Ser Ser Arg Leu Leu Ala Val Gly Asn Pro
                35                  40                  45

Tyr Phe Ser Ile Lys Ser Pro Asn Asn Asn Lys Lys Val Leu Val Pro
50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
                100                 105                 110

Pro Leu Gly Val Gly Val Ser Gly His Pro Tyr Leu Asn Lys Phe Asp
                115                 120                 125

Asp Thr Glu Thr Ser Asn Arg Tyr Pro Ala Gln Pro Gly Ser Asp Asn
                130                 135                 140

Arg Glu Cys Leu Ser Met Asp Tyr Lys Gln Thr Gln Leu Cys Leu Ile
145                 150                 155                 160

Gly Cys Lys Pro Pro Thr Gly Glu His Trp Gly Lys Gly Val Ala Cys
```

165                 170                 175
Asn Asn Asn Ala Ala Thr Asp Cys Pro Leu Glu Leu Phe Asn
            180                 185                 190

Ser Ile Ile Glu Asp Gly Asp Met Val Asp Thr Gly Phe Gly Cys Met
            195                 200                 205

Asp Phe Gly Thr Leu Gln Ala Asn Lys Ser Asp Val Pro Ile Asp Ile
    210                 215                 220

Cys Asn Ser Thr Cys Lys Tyr Pro Asp Tyr Leu Lys Met Ala Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Lys Leu Gly Glu Ala Val Pro
            260                 265                 270

Asp Asp Leu Tyr Ile Lys Gly Ser Gly Asn Thr Ala Val Ile Gln Ser
        275                 280                 285

Ser Ala Phe Phe Pro Thr Pro Ser Gly Ser Ile Val Thr Ser Glu Ser
    290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Thr Leu Cys Thr Glu Val Thr Lys Glu Gly
            340                 345                 350

Thr Tyr Lys Asn Asp Asn Phe Lys Glu Tyr Val Arg His Val Glu Glu
        355                 360                 365

Tyr Asp Leu Gln Phe Val Phe Gln Leu Cys Lys Ile Thr Leu Thr Ala
    370                 375                 380

Glu Ile Met Thr Tyr Ile His Thr Met Asp Ser Asn Ile Leu Glu Asp
385                 390                 395                 400

Trp Gln Phe Gly Leu Thr Pro Pro Ser Ala Ser Leu Gln Asp Thr
                405                 410                 415

Tyr Arg Phe Val Thr Ser Gln Ala Ile Thr Cys Gln Lys Thr Ala Pro
        420                 425                 430

Pro Lys Glu Lys Glu Asp Pro Leu Asn Lys Tyr Thr Phe Trp Glu Val
    435                 440                 445

Asn Leu Lys Glu Lys Phe Ser Ala Asp Leu Asp Gln Phe Pro Leu Gly
    450                 455                 460

Arg Lys Phe Leu Leu Gln Ser Gly Leu Lys Ala Lys Pro Arg Leu Lys
465                 470                 475                 480

Arg Ser Ala Pro Thr Thr Arg Ala Pro Ser Thr Lys Arg Lys Lys Val
                485                 490                 495

Lys Lys

<210> SEQ ID NO 5
<211> LENGTH: 485
<212> TYPE: PRT
<213> ORGANISM: Artificial sequence
<220> FEATURE:
<223> OTHER INFORMATION: Truncated HPV58 L1 protein

<400> SEQUENCE: 5

Met Pro Val Pro Val Ser Lys Val Val Ser Thr Asp Glu Tyr Val Ser
1               5                   10                  15

Arg Thr Ser Ile Tyr Tyr Tyr Ala Gly Ser Ser Arg Leu Leu Ala Val
            20                  25                  30

-continued

```
Gly Asn Pro Tyr Phe Ser Ile Lys Ser Pro Asn Asn Lys Lys Val
         35                  40                  45

Leu Val Pro Lys Val Ser Gly Leu Gln Tyr Arg Val Phe Arg Val Arg
50                  55                  60

Leu Pro Asp Pro Asn Lys Phe Gly Phe Pro Asp Thr Ser Phe Tyr Asn
65                  70                  75                  80

Pro Asp Thr Gln Arg Leu Val Trp Ala Cys Val Gly Leu Glu Ile Gly
                 85                  90                  95

Arg Gly Gln Pro Leu Gly Val Gly Val Ser Gly His Pro Tyr Leu Asn
                100                 105                 110

Lys Phe Asp Asp Thr Glu Thr Ser Asn Arg Tyr Pro Ala Gln Pro Gly
                115                 120                 125

Ser Asp Asn Arg Glu Cys Leu Ser Met Asp Tyr Lys Gln Thr Gln Leu
130                 135                 140

Cys Leu Ile Gly Cys Lys Pro Pro Thr Gly Glu His Trp Gly Lys Gly
145                 150                 155                 160

Val Ala Cys Asn Asn Asn Ala Ala Thr Asp Cys Pro Pro Leu Glu
                165                 170                 175

Leu Phe Asn Ser Ile Ile Glu Asp Gly Asp Met Val Asp Thr Gly Phe
                180                 185                 190

Gly Cys Met Asp Phe Gly Thr Leu Gln Ala Asn Lys Ser Asp Val Pro
                195                 200                 205

Ile Asp Ile Cys Asn Ser Thr Cys Lys Tyr Pro Asp Tyr Leu Lys Met
210                 215                 220

Ala Ser Glu Pro Tyr Gly Asp Ser Leu Phe Phe Leu Arg Arg Glu
225                 230                 235                 240

Gln Met Phe Val Arg His Phe Phe Asn Arg Ala Gly Lys Leu Gly Glu
                245                 250                 255

Ala Val Pro Asp Asp Leu Tyr Ile Lys Gly Ser Gly Asn Thr Ala Val
                260                 265                 270

Ile Gln Ser Ser Ala Phe Phe Pro Thr Pro Ser Gly Ser Ile Val Thr
                275                 280                 285

Ser Glu Ser Gln Leu Phe Asn Lys Pro Tyr Trp Leu Gln Arg Ala Gln
                290                 295                 300

Gly His Asn Asn Gly Ile Cys Trp Gly Asn Gln Leu Phe Val Thr Val
305                 310                 315                 320

Val Asp Thr Thr Arg Ser Thr Asn Met Thr Leu Cys Thr Glu Val Thr
                325                 330                 335

Lys Glu Gly Thr Tyr Lys Asn Asp Asn Phe Lys Glu Tyr Val Arg His
                340                 345                 350

Val Glu Glu Tyr Asp Leu Gln Phe Val Phe Gln Leu Cys Lys Ile Thr
                355                 360                 365

Leu Thr Ala Glu Ile Met Thr Tyr Ile His Thr Met Asp Ser Asn Ile
370                 375                 380

Leu Glu Asp Trp Gln Phe Gly Leu Thr Pro Pro Pro Ser Ala Ser Leu
385                 390                 395                 400

Gln Asp Thr Tyr Arg Phe Val Thr Ser Gln Ala Ile Thr Cys Gln Lys
                405                 410                 415

Thr Ala Pro Pro Lys Glu Lys Glu Asp Pro Leu Asn Lys Tyr Thr Phe
                420                 425                 430

Trp Glu Val Asn Leu Lys Glu Lys Phe Ser Ala Asp Leu Asp Gln Phe
                435                 440                 445
```

```
Pro Leu Gly Arg Lys Phe Leu Leu Gln Ser Gly Leu Lys Ala Lys Pro
    450                 455                 460

Arg Leu Lys Arg Ser Ala Pro Thr Thr Arg Ala Pro Ser Thr Lys Arg
465                 470                 475                 480

Lys Lys Val Lys Lys
            485

<210> SEQ ID NO 6
<211> LENGTH: 465
<212> TYPE: PRT
<213> ORGANISM: Artificial sequence
<220> FEATURE:
<223> OTHER INFORMATION: Truncated HPV58 L1 protein

<400> SEQUENCE: 6

Met Tyr Tyr Ala Gly Ser Ser Arg Leu Leu Ala Val Gly Asn Pro Tyr
1               5                   10                  15

Phe Ser Ile Lys Ser Pro Asn Asn Lys Val Leu Val Pro Lys
            20                  25                  30

Val Ser Gly Leu Gln Tyr Arg Val Phe Arg Val Arg Leu Pro Asp Pro
            35                  40                  45

Asn Lys Phe Gly Phe Pro Asp Thr Ser Phe Tyr Asn Pro Asp Thr Gln
50                  55                  60

Arg Leu Val Trp Ala Cys Val Gly Leu Glu Ile Gly Arg Gly Gln Pro
65                  70                  75                  80

Leu Gly Val Gly Val Ser Gly His Pro Tyr Leu Asn Lys Phe Asp Asp
                85                  90                  95

Thr Glu Thr Ser Asn Arg Tyr Pro Ala Gln Pro Gly Ser Asp Asn Arg
            100                 105                 110

Glu Cys Leu Ser Met Asp Tyr Lys Gln Thr Gln Leu Cys Leu Ile Gly
            115                 120                 125

Cys Lys Pro Pro Thr Gly Glu His Trp Gly Lys Gly Val Ala Cys Asn
130                 135                 140

Asn Asn Ala Ala Ala Thr Asp Cys Pro Pro Leu Glu Leu Phe Asn Ser
145                 150                 155                 160

Ile Ile Glu Asp Gly Asp Met Val Asp Thr Gly Phe Gly Cys Met Asp
                165                 170                 175

Phe Gly Thr Leu Gln Ala Asn Lys Ser Asp Val Pro Ile Asp Ile Cys
            180                 185                 190

Asn Ser Thr Cys Lys Tyr Pro Asp Tyr Leu Lys Met Ala Ser Glu Pro
            195                 200                 205

Tyr Gly Asp Ser Leu Phe Phe Phe Leu Arg Arg Glu Gln Met Phe Val
210                 215                 220

Arg His Phe Phe Asn Arg Ala Gly Lys Leu Gly Glu Ala Val Pro Asp
225                 230                 235                 240

Asp Leu Tyr Ile Lys Gly Ser Gly Asn Thr Ala Val Ile Gln Ser Ser
                245                 250                 255

Ala Phe Phe Pro Thr Pro Ser Gly Ser Ile Val Thr Ser Glu Ser Gln
            260                 265                 270

Leu Phe Asn Lys Pro Tyr Trp Leu Gln Arg Ala Gln Gly His Asn Asn
            275                 280                 285

Gly Ile Cys Trp Gly Asn Gln Leu Phe Val Thr Val Asp Thr Thr
290                 295                 300

Arg Ser Thr Asn Met Thr Leu Cys Thr Glu Val Thr Lys Glu Gly Thr
305                 310                 315                 320
```

Tyr Lys Asn Asp Asn Phe Lys Glu Tyr Val Arg His Val Glu Glu Tyr
            325             330             335

Asp Leu Gln Phe Val Phe Gln Leu Cys Lys Ile Thr Leu Thr Ala Glu
        340             345             350

Ile Met Thr Tyr Ile His Thr Met Asp Ser Asn Ile Leu Glu Asp Trp
            355             360             365

Gln Phe Gly Leu Thr Pro Pro Ser Ala Ser Leu Gln Asp Thr Tyr
370             375             380

Arg Phe Val Thr Ser Gln Ala Ile Thr Cys Gln Lys Thr Ala Pro Pro
385             390             395             400

Lys Glu Lys Glu Asp Pro Leu Asn Lys Tyr Thr Phe Trp Glu Val Asn
            405             410             415

Leu Lys Glu Lys Phe Ser Ala Asp Leu Asp Gln Phe Pro Leu Gly Arg
            420             425             430

Lys Phe Leu Leu Gln Ser Gly Leu Lys Ala Lys Pro Arg Leu Lys Arg
            435             440             445

Ser Ala Pro Thr Thr Arg Ala Pro Ser Thr Lys Arg Lys Lys Val Lys
    450             455             460

Lys
465

<210> SEQ ID NO 7
<211> LENGTH: 455
<212> TYPE: PRT
<213> ORGANISM: Artificial sequence
<220> FEATURE:
<223> OTHER INFORMATION: Truncated HPV58 L1 protein

<400> SEQUENCE: 7

Met Val Gly Asn Pro Tyr Phe Ser Ile Lys Ser Pro Asn Asn Lys
1               5                   10                  15

Lys Val Leu Val Pro Lys Val Ser Gly Leu Gln Tyr Arg Val Phe Arg
            20              25                  30

Val Arg Leu Pro Asp Pro Asn Lys Phe Gly Phe Pro Asp Thr Ser Phe
        35              40                  45

Tyr Asn Pro Asp Thr Gln Arg Leu Val Trp Ala Cys Val Gly Leu Glu
    50              55                  60

Ile Gly Arg Gly Gln Pro Leu Gly Val Gly Val Ser Gly His Pro Tyr
65              70                  75                  80

Leu Asn Lys Phe Asp Asp Thr Glu Thr Ser Asn Arg Tyr Pro Ala Gln
            85                  90                  95

Pro Gly Ser Asp Asn Arg Glu Cys Leu Ser Met Asp Tyr Lys Gln Thr
            100                 105                 110

Gln Leu Cys Leu Ile Gly Cys Lys Pro Pro Thr Gly Glu His Trp Gly
        115             120                 125

Lys Gly Val Ala Cys Asn Asn Asn Ala Ala Thr Asp Cys Pro Pro
130                 135                 140

Leu Glu Leu Phe Asn Ser Ile Ile Glu Asp Gly Asp Met Val Asp Thr
145                 150                 155                 160

Gly Phe Gly Cys Met Asp Phe Gly Thr Leu Gln Ala Asn Lys Ser Asp
            165                 170                 175

Val Pro Ile Asp Ile Cys Asn Ser Thr Cys Lys Tyr Pro Asp Tyr Leu
        180                 185                 190

Lys Met Ala Ser Glu Pro Tyr Gly Asp Ser Leu Phe Phe Phe Leu Arg
            195                 200                 205

Arg Glu Gln Met Phe Val Arg His Phe Phe Asn Arg Ala Gly Lys Leu
            210                 215                 220

Gly Glu Ala Val Pro Asp Asp Leu Tyr Ile Lys Gly Ser Gly Asn Thr
225                 230                 235                 240

Ala Val Ile Gln Ser Ser Ala Phe Phe Pro Thr Pro Ser Gly Ser Ile
                245                 250                 255

Val Thr Ser Glu Ser Gln Leu Phe Asn Lys Pro Tyr Trp Leu Gln Arg
            260                 265                 270

Ala Gln Gly His Asn Asn Gly Ile Cys Trp Gly Asn Gln Leu Phe Val
        275                 280                 285

Thr Val Val Asp Thr Thr Arg Ser Thr Asn Met Thr Leu Cys Thr Glu
290                 295                 300

Val Thr Lys Glu Gly Thr Tyr Lys Asn Asp Asn Phe Lys Glu Tyr Val
305                 310                 315                 320

Arg His Val Glu Glu Tyr Asp Leu Gln Phe Val Phe Gln Leu Cys Lys
                325                 330                 335

Ile Thr Leu Thr Ala Glu Ile Met Thr Tyr Ile His Thr Met Asp Ser
            340                 345                 350

Asn Ile Leu Glu Asp Trp Gln Phe Gly Leu Thr Pro Pro Pro Ser Ala
                355                 360                 365

Ser Leu Gln Asp Thr Tyr Arg Phe Val Thr Ser Gln Ala Ile Thr Cys
        370                 375                 380

Gln Lys Thr Ala Pro Pro Lys Glu Lys Glu Asp Pro Leu Asn Lys Tyr
385                 390                 395                 400

Thr Phe Trp Glu Val Asn Leu Lys Glu Lys Phe Ser Ala Asp Leu Asp
                405                 410                 415

Gln Phe Pro Leu Gly Arg Lys Phe Leu Leu Gln Ser Gly Leu Lys Ala
            420                 425                 430

Lys Pro Arg Leu Lys Arg Ser Ala Pro Thr Thr Arg Ala Pro Ser Thr
                435                 440                 445

Lys Arg Lys Lys Val Lys Lys
            450                 455

<210> SEQ ID NO 8
<211> LENGTH: 1575
<212> TYPE: DNA
<213> ORGANISM: HPV58

<400> SEQUENCE: 8
atggtgctga tcctgtgctg caccctggcc atcctgttct gcgtggccga cgtgaacgtg      60
ttccacatct tcctgcagat gagcgtgtgg aggcccagcg aggccaccgt gtacctgccc     120
cccgtgcccg tgagcaaggt ggtgagcacc gacgagtacg tgagcaggac cagcatctac     180
tactacgccg gcagcagcag gctgctggcc gtgggcaacc cctacttcag catcaagagc     240
cccaacaaca caagaaggt gctggtgccc aaggtgagcg gcctgcagta cagggtgttc     300
agggtgaggc tgcccgaccc caacaagttc ggcttccccg acaccagctt ctacaacccc     360
gacacccaga ggctggtgtg ggcctgcgtg ggcctggaga tcggcagggg ccagccctg      420 ggcgtgggcg tgagcggcca ccctacctg aacaagttcg acgacaccga gaccagcaac     480
aggtaccccg cccagcccgg cagcgacaac agggagtgcc tgagcatgga ctacaagcag     540
acccagctgt gcctgatcgg ctgcaagccc cccaccggcg agcactgggg caagggcgtg     600
gcctgcaaca caacgccgc cgccaccgac tgccccccc tggagctgtt caacagcatc     660
atcgaggacg gcgacatggt ggacaccggc ttcggctgca tggacttcgg caccctgcag     720

```
gccaacaaga gcgacgtgcc catcgacatc tgcaacagca cctgcaagta ccccgactac    780
ctgaagatgg ccagcgagcc ctacggcgac agcctgttct tcttcctgag agggagcag    840 atgttcgtga ggcacttctt caacagggcc ggcaagctgg gcgaggccgt gcccgacgac    900
ctgtacatca agggcagcgg caacaccgcc gtgatccaga gcagcgcctt cttccccacc    960
cccagcggca gcatcgtgac cagcgagagc cagctgttca caagccccta ctggctgcag   1020
agggcccagg ccacaacaa cggcatctgc tggggcaacc agctgttcgt gaccgtggtg   1080
gacaccacca ggagcaccaa catgaccctg tgcaccgagg tgaccaagga gggcacctac   1140
aagaacgaca acttcaagga gtacgtgagg cacgtggaga gtacgacct gcagttcgtg    1200 ttccagctgt gcaagatcac cctgaccgcc gagatcatga cctacatcca ccatggac    1260 agcaacatcc tggaggactg gcagttcggc ctgacccccc ccccagcgc cagcctgcag    1320 gacacctaca ggttcgtgac cagccaggcc atcacctgcc agaagaccgc cccccccaag    1380
gagaaggagg accccctgaa caagtacacc ttctgggagg tgaacctgaa ggagaagttc   1440
agcgccgacc tggaccagtt cccctgggc aggaagttcc tgctgcagag cggcctgaag   1500
gccaagccca ggctgaagag gagcgccccc accaccaggg ccccagcac caagaggaag   1560 aaggtgaaga agtga                                                   1575
```

<210> SEQ ID NO 9
<211> LENGTH: 1473
<212> TYPE: DNA
<213> ORGANISM: Artificial sequence
<220> FEATURE:
<223> OTHER INFORMATION: Truncated HPV58 L1 gene

<400> SEQUENCE: 9

```
atgaccgtgt acctgccccc cgtgcccgtg agcaaggtgg tgagcaccga cgagtacgtg     60
agcaggacca gcatctacta ctacgccggc agcagcaggc tgctggccgt gggcaacccc    120
tacttcagca tcaagagccc caacaacaac aagaaggtgc tggtgcccaa ggtgagcggc    180
ctgcagtaca gggtgttcag ggtgaggctg cccgacccca caagttcgg cttccccgac    240 accagcttct acaaccccga cacccagagg ctggtgtggg cctgcgtggg cctggagatc    300
ggcagggccc agccctggg cgtgggcgtg agcggccacc cctacctgaa caagttcgac    360
gacaccgaga ccagcaacag gtaccccgcc cagcccggca gcgacaacag ggagtgcctg    420
agcatggact acaagcagac ccagctgtgc ctgatcggct gcaagccccc caccggcgag    480
cactggggca agggcgtggc ctgcaacaac aacgccgccg ccaccgactg cccccccctg    540
gagctgttca acagcatcat cgaggacggc gacatggtgg acaccggctt cggctgcatg    600
gacttcggca ccctgcaggc caacaagagc gacgtgccca tcgacatctg caacagcacc    660
tgcaagtacc ccgactacct gaagatggcc agcgagccct acggcgacag cctgttcttc    720
ttcctgagga gggagcagat gttcgtgagg cacttcttca cagggccgg caagctgggc    780 gaggccgtgc ccgacgacct gtacatcaag ggcagcggca acaccgccgt gatccagagc    840
agcgccttct cccccacccc cagcggcagc atcgtgacca gcgagagcca gctgttcaac    900 aagcccact ggctgcagag ggcccaggc cacaacaacg gcatctgctg gggcaaccag    960
ctgttcgtga ccgtggtgga caccaccagg agcaccaaca tgaccctgtg caccgaggtg   1020
accaaggagg gcacctacaa gaacgacaac ttcaaggagt acgtgaggca cgtggaggag   1080
tacgacctgc agttcgtgtt ccagctgtgc aagatcaccc tgaccgccga gatcatgacc   1140
```

```
tacatccaca ccatggacag caacatcctg gaggactggc agttcggcct gaccccccc     1200 cccagcgcca gcctgcagga cacctacagg ttcgtgacca gccaggccat cacctgccag     1260
aagaccgccc cccccaagga aaggaggac cccctgaaca agtacacctt ctgggaggtg      1320
aacctgaagg agaagttcag cgccgacctg gaccagttcc ccctgggcag gaagttcctg     1380
ctgcagagcg gcctgaaggc caagcccagg ctgaagagga gcgcccccac caccagggcc     1440
cccagcacca agaggaagaa ggtgaagaag taa                                  1473
```

```
<210> SEQ ID NO 10
<211> LENGTH: 1563
<212> TYPE: DNA
<213> ORGANISM: Artificial sequence
<220> FEATURE:
<223> OTHER INFORMATION: Truncated HPV58 L1 gene

<400> SEQUENCE: 10
atgtgctgca ccctggccat cctgttctgc gtggccgacg tgaacgtgtt ccacatcttc      60
ctgcagatga gcgtgtggag gcccagcgag gccaccgtgt acctgccccc cgtgcccgtg     120
agcaaggtgg tgagcaccga cgagtacgtg agcaggacca gcatctacta ctacgccggc     180
agcagcaggc tgctggccgt gggcaacccc tacttcagca tcaagagccc caacaacaac     240
aagaaggtgc tggtgcccaa ggtgagcggc ctgcagtaca gggtgttcag ggtgaggctg     300
cccgacccca caagttcgg cttccccgac ccagcttct acaaccccga cacccagagg       360
ctggtgtggg cctgcgtggg cctggagatc ggcaggggcc agcccctggg cgtgggcgtg     420
agcggccacc cctacctgaa caagttcgac gacaccgaga ccagcaacag gtaccccgcc     480
cagcccggca gcgacaacag ggagtgcctg agcatggact acaagcagac ccagctgtgc     540
ctgatcggct gcaagccccc caccggcgag cactggggca agggcgtggc ctgcaacaac     600
aacgccgccg ccaccgactg cccccccctg agctgttca acagcatcat cgaggacggc     660
gacatggtgg acaccggctt cggctgcatg gacttcggca ccctgcaggc caacaagagc    720
gacgtgccca tcgacatctg caacagcacc tgcaagtacc ccgactacct gaagatggcc    780 agcgagcct acgcgacag cctgttcttc ttcctgagga gggagcagat gttcgtgagg      840
cacttcttca cagggccgg caagctgggc gaggccgtgc ccgacgacct gtacatcaag     900
ggcagcggca acaccgccgt gatccagagc agcgccttct tccccacccc cagcggcagc    960
atcgtgacca gcgagagcca gctgttcaac aagccctact ggctgcagag ggcccagggc    1020
cacaacaacg gcatctgctg gggcaaccag ctgttcgtga ccgtggtgga caccaccagg    1080
agcaccaaca tgaccctgtg caccgaggtg accaaggagg gcacctacaa gaacgacaac    1140
ttcaaggagt acgtgaggca cgtggaggag tacgacctgc agttcgtgtt ccagctgtgc    1200
aagatcaccc tgaccgccga gatcatgacc tacatccaca ccatggacag caacatcctg    1260
gaggactggc agttcggcct gacccccccc cccagcgcca gcctgcagga cacctacagg    1320
ttcgtgacca gccaggccat cacctgccag aagaccgccc cccccaagga aaggaggac     1380 cccctgaaca agtacacctt ctgggaggtg aacctgaagg agaagttcag cgccgacctg    1440
gaccagttcc ccctgggcag gaagttcctg ctgcagagcg gcctgaaggc caagcccagg    1500
ctgaagagga gcgcccccac caccagggcc cccagcacca agaggaagaa ggtgaagaag    1560
tga                                                                  1563
```

```
<210> SEQ ID NO 11
<211> LENGTH: 1533
```

<212> TYPE: DNA
<213> ORGANISM: Artificial sequence
<220> FEATURE:
<223> OTHER INFORMATION: Truncated HPV58 L1 gene

<400> SEQUENCE: 11

```
atggccgacg tgaacgtgtt ccacatcttc ctgcagatga gcgtgtggag gcccagcgag     60
gccaccgtgt acctgccccc cgtgcccgtg agcaaggtgg tgagcaccga cgagtacgtg    120
agcaggacca gcatctacta ctacgccggc agcagcaggc tgctggccgt gggcaacccc    180
tacttcagca tcaagagccc caacaacaac aagaaggtgc tggtgcccaa ggtgagcggc    240
ctgcagtaca gggtgttcag ggtgaggctg cccgacccca caagttcgg cttccccgac     300
accagcttct acaaccccga cacccagagg ctggtgtggg cctgcgtggg cctggagatc    360
ggcaggggcc agcccctggg cgtgggcgtg agcggccacc cctacctgaa caagttcgac    420
gacaccgaga ccagcaacag gtaccccgcc cagcccggca gcgacaacag ggagtgcctg    480
agcatggact acaagcagac ccagctgtgc ctgatcggct gcaagccccc caccggcgag    540
cactggggca agggcgtggc ctgcaacaac aacgccgccg ccaccgactg ccccccctg     600
gagctgttca acagcatcat cgaggacggc gacatggtgg acaccggctt cggctgcatg    660
gacttcggca ccctgcaggc caacaagagc gacgtgccca tcgacatctg caacagcacc    720
tgcaagtacc ccgactacct gaagatggcc agcgagccct acggcgacag cctgttcttc    780
ttcctgagga gggagcagat gttcgtgagg cacttcttca cagggccgg caagctgggc     840
gaggccgtgc ccgacgacct gtacatcaag ggcagcggca caccgccgt gatccagagc     900
agcgccttct tccccacccc cagcggcagc atcgtgacca gcgagagcca gctgttcaac    960
aagccctact ggctgcagag ggcccagggc cacaacaacg gcatctgctg gggcaaccag   1020
ctgttcgtga ccgtggtgga caccaccagg agcaccaaca tgacccgtgt caccgaggtg   1080
accaaggagg gcacctacaa gaacgacaac ttcaaggagt acgtgaggca cgtggaggag   1140
tacgacctgc agttcgtgtt ccagctgtgc aagatcaccc tgaccgccga gatcatgacc   1200
tacatccaca ccatggacag caacatcctg gaggactggc agttcggcct gacccccccc   1260
cccagcgcca gcctgcagga cacctacagg ttcgtgacca gccaggccat cacctgccag   1320
aagaccgccc cccccaagga gaaggaggac cccctgaaca gtacaccttc tggggaggtg   1380
aacctgaagg agaagttcag cgccgacctg gaccagttcc cctgggcag gaagttcctg     1440
ctgcagagcg gcctgaaggc caagcccagg ctgaagagga gcgcccccac caccagggcc   1500
cccagcacca gaggaagaa ggtgaagaag tga                                  1533
```

<210> SEQ ID NO 12
<211> LENGTH: 1497
<212> TYPE: DNA
<213> ORGANISM: Artificial sequence
<220> FEATURE:
<223> OTHER INFORMATION: Truncated HPV58 L1 gene

<400> SEQUENCE: 12

```
atgagcgtgt ggaggcccag cgaggccacc gtgtacctgc ccccgtgcc cgtgagcaag      60
gtggtgagca ccgacgagta cgtgagcagg accagcatct actactacgc cggcagcagc    120
aggctgctgg ccgtgggcaa cccctacttc agcatcaaga gccccaacaa caacaagaag    180
gtgctggtgc ccaaggtgag cggcctgcag tacagggtgt tcagggtgag gctgcccgac    240
cccaacaagt tcggcttccc cgacaccagc ttctacaacc ccgacaccca gaggctggtg    300
```

| | |
|---|---|
| tgggcctgcg tgggcctgga gatcggcagg ggccagcccc tgggcgtggg cgtgagcggc | 360 |
| caccccctacc tgaacaagtt cgacgacacc gagaccagca acaggtaccc cgcccagccc | 420 |
| ggcagcgaca cagggagtg cctgagcatg gactacaagc agacccagct gtgcctgatc | 480 |
| ggctgcaagc cccccaccgg cgagcactgg ggcaagggcg tggcctgcaa caacaacgcc | 540 |
| gccgccaccg actgcccccc cctggagctg ttcaacagca tcatcgagga cggcgacatg | 600 |
| gtggacaccg gcttcggctg catggacttc ggcaccctgc aggccaacaa gagcgacgtg | 660 |
| cccatcgaca tctgcaacag cacctgcaag taccccgact acctgaagat ggccagcgag | 720 |
| ccctacggcg acagcctgtt cttcttcctg aggagggagc agatgttcgt gaggcacttc | 780 |
| ttcaacaggg ccggcaagct gggcgaggcc gtgcccgacg acctgtacat caagggcagc | 840 |
| ggcaacaccg ccgtgatcca gagcagcgcc ttcttcccca ccccagcgg cagcatcgtg | 900 |
| accagcgaga gccagctgtt caacaagccc tactggctgc agagggccca gggccacaac | 960 |
| aacggcatct gctggggcaa ccagctgttc gtgaccgtgg tggacaccac caggagcacc | 1020 |
| aacatgaccc tgtgcaccga ggtgaccaag gagggcacct acaagaacga caacttcaag | 1080 |
| gagtacgtga ggcacgtgga ggagtacgac ctgcagttcg tgttccagct gtgcaagatc | 1140 |
| accctgaccg ccgagatcat gacctacatc cacaccatgg acagcaacat cctggaggac | 1200 |
| tggcagttcg gcctgacccc ccccccagc gccagcctgc aggacaccta caggttcgtg | 1260 |
| accagccagg ccatcacctg ccagaagacc gccccccca aggagaagga ggaccccctg | 1320 |
| aacaagtaca ccttctggga ggtgaacctg aaggagaagt cagcgccga cctggaccag | 1380 |
| ttcccccctgg gcaggaagtt cctgctgcag agcggcctga aggccaagcc caggctgaag | 1440 |
| aggagcgccc ccaccaccag ggccccagc accaagagga gaaggtgaa gaagtga | 1497 |

<210> SEQ ID NO 13
<211> LENGTH: 1458
<212> TYPE: DNA
<213> ORGANISM: Artificial sequence
<220> FEATURE:
<223> OTHER INFORMATION: Truncated HPV58 L1 gene

<400> SEQUENCE: 13

| | |
|---|---|
| atgcccgtgc ccgtgagcaa ggtggtgagc accgacgagt acgtgagcag gaccagcatc | 60 |
| tactactacg ccggcagcag caggctgctg gccgtgggca cccctactt cagcatcaag | 120 |
| agccccaaca caacaagaa ggtgctggtg cccaaggtga gcggcctgca gtacagggtg | 180 |
| ttcagggtga ggctgcccga ccccaacaag ttcggcttcc ccgacaccag cttctacaac | 240 |
| cccgacaccc agaggctggt gtgggcctgc gtgggcctgg agatcggcag gggccagccc | 300 |
| ctgggcgtgg gcgtgagcgg ccaccccctac ctgaacaagt cgacgacac cgagaccagc | 360 |
| aacaggtacc ccgcccagcc cggcagcgac aacagggagt gcctgagcat ggactacaag | 420 |
| cagacccagc tgtgcctgat cggctgcaag ccccccaccg gcgagcactg ggcaagggc | 480 |
| gtggcctgca acaacaacgc cgccgccacc gactgccccc cctggagct gttcaacagc | 540 |
| atcatcgagg acggcgacat ggtggacacc ggcttcggct gcatggactt cggcaccctg | 600 |
| caggccaaca agagcgacgt gcccatcgac atctgcaaca gcacctgcaa gtaccccgac | 660 |
| tacctgaaga tggccagcga gccctacggc gacagcctgt tcttcttcct gaggagggag | 720 |
| cagatgttcg tgaggcactt cttcaacagg gccggcaagc tgggcgaggc cgtgcccgac | 780 |
| gacctgtaca tcaagggcag cggcaacacc gccgtgatcc agagcagcgc cttcttcccc | 840 |
| accccagcg gcagcatcgt gaccagcgag agccagctgt tcaacaagcc ctactggctg | 900 |

```
cagagggccc agggccacaa caacggcatc tgctggggca accagctgtt cgtgaccgtg    960
gtggacacca ccaggagcac caacatgacc ctgtgcaccg aggtgaccaa ggagggcacc   1020
tacaagaacg acaacttcaa ggagtacgtg aggcacgtgg aggagtacga cctgcagttc   1080
gtgttccagc tgtgcaagat caccctgacc gccgagatca tgacctacat ccacaccatg   1140
gacagcaaca tcctggagga ctggcagttc ggcctgaccc ccccccccag cgccagcctg   1200
caggacacct acaggttcgt gaccagccag gccatcacct gccagaagac cgccccccc   1260 aaggagaagg aggacccct gaacaagtac accttctggg aggtgaacct gaaggagaag   1320
ttcagcgccg acctggacca gttccccctg ggcaggaagt tcctgctgca gagcggcctg   1380
aaggccaagc ccaggctgaa gaggagcgcc cccaccacca gggcccccag caccaagagg   1440
aagaaggtga agaagtaa                                                 1458

<210> SEQ ID NO 14
<211> LENGTH: 1398
<212> TYPE: DNA
<213> ORGANISM: Artificial sequence
<220> FEATURE:
<223> OTHER INFORMATION: Truncated HPV58 L1 gene

<400> SEQUENCE: 14
atgtactacg ccggcagcag caggctgctg gccgtgggca acccctactt cagcatcaag     60
agccccaaca caacaagaa ggtgctggtg cccaaggtga gcggcctgca gtacagggtg    120
ttcagggtga ggctgcccga ccccaacaag ttcggcttcc ccgacaccag cttctacaac    180
cccgacaccc agaggctggt gtgggcctgc gtgggcctgg agatcggcag ggggccagccc   240 ctgggcgtgg gcgtgagcgg ccaccccctac ctgaacaagt cgacgacac cgagaccagc    300 aacaggtacc ccgcccagcc cggcagcgac aacagggagt gcctgagcat ggactacaag    360
cagacccagc tgtgcctgat cggctgcaag cccccccacg cgagcactg ggcaagggc    420 gtggcctgca acaacaacgc cgccgccacc gactgccccc ccctggagct gttcaacagc    480
atcatcgagg acggcgacat ggtggacacc ggcttcggct gcatggactt cggcaccctg    540
caggccaaca gagcgacgt gcccatcgac atctgcaaca gcacctgcaa gtaccccgac    600
tacctgaaga tggccagcga gccctacggc gacagcctgt tcttcttcct gaggagggag    660
cagatgttcg tgaggcactt cttcaacagg gccggcaagt gggcgaggc cgtgcccgac    720 gacctgtaca tcaagggcag cggcaacacc gccgtgatcc agagcagcgc cttcttcccc    780 accccagcg gcagcatcgt gaccagcgag agccagctgt tcaacaagcc ctactggctg    840
cagagggccc agggccacaa caacggcatc tgctggggca accagctgtt cgtgaccgtg    900
gtggacacca ccaggagcac caacatgacc ctgtgcaccg aggtgaccaa ggagggcacc    960
tacaagaacg acaacttcaa ggagtacgtg aggcacgtgg aggagtacga cctgcagttc   1020
gtgttccagc tgtgcaagat caccctgacc gccgagatca tgacctacat ccacaccatg   1080
gacagcaaca tcctggagga ctggcagttc ggcctgaccc ccccccccag cgccagcctg   1140
caggacacct acaggttcgt gaccagccag gccatcacct gccagaagac cgccccccc   1200 aaggagaagg aggacccct gaacaagtac accttctggg aggtgaacct gaaggagaag   1260
ttcagcgccg acctggacca gttccccctg ggcaggaagt tcctgctgca gagcggcctg   1320
aaggccaagc ccaggctgaa gaggagcgcc cccaccacca gggcccccag caccaagagg   1380
aagaaggtga agaagtga                                                 1398
```

```
<210> SEQ ID NO 15
<211> LENGTH: 1368
<212> TYPE: DNA
<213> ORGANISM: Artificial sequence
<220> FEATURE:
<223> OTHER INFORMATION: Truncated HPV58 L1 gene

<400> SEQUENCE: 15
atggtgggca acccctactt cagcatcaag agccccaaca acaacaagaa ggtgctggtg      60
cccaaggtga gcggcctgca gtacagggtg ttcagggtga ggctgcccga ccccaacaag     120
ttcggcttcc ccgacaccag cttctacaac cccgacaccc agaggctggt gtgggcctgc     180
gtgggcctgg agatcggcag gggccagccc tgggcgtgg gcgtgagcgg ccaccccta     240 ctgaacaagt tcgacgacac cgagaccagc aacaggtacc ccgcccagcc cggcagcgac     300
aacagggagt gcctgagcat ggactacaag cagacccagc tgtgcctgat cggctgcaag     360
ccccccaccg gcgagcactg gggcaagggc gtggcctgca caacaacgc cgccgccacc     420 gactgccccc cctggagct gttcaacagc atcatcgagg acggcgacat ggtggacacc     480
ggcttcggct gcatggactt cggcaccctg caggccaaca gagcgacgt gcccatcgac     540 atctgcaaca gcacctgcaa gtaccccgac tacctgaaga tggccagcga gccctacggc     600
gacagcctgt tcttcttcct gaggagggag cagatgttcg tgaggcactt cttcaacagg     660
gccggcaagc tgggcgaggc cgtgcccgac gacctgtaca tcaagggcag cggcaacacc     720
gccgtgatcc agagcagcgc cttcttcccc acccccagcg gcagcatcgt gaccagcgag     780
agccagctgt tcaacaagcc ctactggctg cagagggccc agggccacaa caacggcatc     840
tgctggggca ccagctgtt cgtgaccgtg gtggacacca ccaggagcac caacatgacc     900
ctgtgcaccg aggtgaccaa ggagggcacc tacaagaacg acaacttcaa ggagtacgtg     960
aggcacgtgg aggagtacga cctgcagttc gtgttccagc tgtgcaagat caccctgacc    1020
gccgagatca tgacctacat ccacaccatg gacagcaaca tcctggagga ctggcagttc    1080
ggcctgaccc ccccccccag cgccagcctg caggacacct acaggttcgt gaccagccag    1140
gccatcacct gccagaagac cgcccccccc aaggagaagg aggacccct gaacaagtac    1200 accttctggg aggtgaacct gaaggagaag ttcagcgccg acctggacca gttcccctg    1260 ggcaggaagt tcctgctgca gagcggcctg aaggccaagc ccaggctgaa gaggagcgcc    1320
cccaccacca gggccccag caccaagagg aagaaggtga agaagtga                  1368

<210> SEQ ID NO 16
<211> LENGTH: 21
<212> TYPE: DNA
<213> ORGANISM: Artificial sequence
<220> FEATURE:
<223> OTHER INFORMATION: primer

<400> SEQUENCE: 16
catatgaccg tgtacctgcc c                                                21

<210> SEQ ID NO 17
<211> LENGTH: 26
<212> TYPE: DNA
<213> ORGANISM: Artificial sequence
<220> FEATURE:
<223> OTHER INFORMATION: primer

<400> SEQUENCE: 17
gtcgacttac ttcttcacct tcttcc                                           26
```

TRUNCATED L1 PROTEIN OF HUMAN PAPILLOMAVIRUS TYPE 58

This application incorporates by reference the contents of a 45.9 kb text file created on Feb. 4, 2016 and named "sequencelisting.txt," which is the sequence listing for this application.

FIELD OF THE INVENTION

The invention relates to the field of molecular virology and immunology. In particular, the invention relates to a truncated L1 protein of Human Papillomavirus Type 58, its coding sequence and preparation method, and a virus-like particle comprising the protein, wherein the protein and the virus-like particle are useful for preventing HPV (particularly HPV58) infection, and a disease caused by HPV (particularly HPV58) infection, such as cervical cancer. The invention also relates to the use of the protein and the virus-like particle in the preparation of a pharmaceutical composition or a vaccine for preventing HPV (particularly HPV58) infection, and a disease caused by HPV (particularly HPV58) infection, such as cervical cancer.

BACKGROUND OF THE INVENTION

Human Papillomavirus (HPV), a non-enveloped, deoxyribonucleic acid (DNA) virus, belongs to the family Papillomaviridae. The viral genome is a double-stranded, closed circular DNA, which is approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4~E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 bp in length, and comprising regulator elements for DNA replication and expression instead of coding for proteins. HPV viral particles have a diameter of 45-55 nm, wherein the nucleocapsid, consisting of L1 and L2, exhibits icosahedral symmetry and comprises 72 capsomers.

Currently, there are over 100 different types of HPV, mainly causing papillary disease in the skin and mucosa of human. HPV types are divided into three groups depending on their relation with tumorigenesis: (1) group of low or no cancerogenic risk, containing HPV 6, 11, 39, 41, 42, and 43; (2) group of medium cancerogenic risk, containing HPV 31, 33, 35, 51 and 52; and (3) group of high cancerogenic risk, containing HPV 16, 18, 58, and 45.

HPV molecular epidemiological investigation demonstrates that infection by high-risk HPV types is an important factor responsible for the development of cervical cancer. Among all the cervical cancer specimens, HPV DNA is detected in over 80% of them. Cervical cancer is a common malignant tumor among women, the incidence of which is only next to breast cancer, and seriously threatens the health of women. There are about 490,000 newly reported cases worldwide every year, and nearly 270,000 people die of this disease annually (Boyle, P., and J. Ferlay. Ann Oncol 2005, 16:481-8). Cases in developing countries account for approximately 83% of the total cervical cancer cases. In these developing countries, the cervical cancer cases account for about 15% of female malignant tumors, in contrast to 1.5% in developed countries. Cervical cancer is most prevalent in sub-Saharan Africa, central and Southern Asia, Latin America, and Eastern Asia. Cervical cancer is also prevalent in China. The incidence of cervical cancer among married women is as high as 1026/100000 in Lueyang County of Shanxi Province.

Meta-analysis of the distribution of HPV types in the worldwide cervical cancer specimens shows that the most common HPV types found in cervical cancer specimens are HPV 16, 18, 45, 31, 33, 58, 52, 35, 59, 56, 6, 51, 68, 39, 82, 73, 66 and 70 (listed in descending order, Clifford G M, Smith J S, Plummer M, et al. Br J Cancer, 2003, 88(1): 63-73).

However, the distribution of HPV types exhibits some characteristics of geographical distribution and populations. In particular, the infection rate of HPV58 in Asia is higher than that in developed countries such as in European and America. Recently, an investigation on the HPV types infected in Chinese women shows that among cervical cancer patients, the infection rate of HPV58 is 7.2%, preceded only by HPV16 (58.7%) and HPV18 (11.0%), and among women with high-grade squamous epithelial lesion or low-grade squamous epithelial lesion and normal women, the infection rate of HPV58 is preceded only by HPV16 (Y P Bao, N Li, J S Smith and Y L Qiao. International Journal of STD & AIDS, 2008, 19: 106-111). This suggests that the infection rate of HPV58 in Chinese women is higher than the worldwide level, and that HPV58 is a HPV type to which Chinese women and Asian women are generally susceptible.

Currently, the commercially available HPV vaccines are GADASIL® from Merck and CERVARIX® from GSK, which comprise HPV6/11/16/18 and HPV16/18 VLP, respectively, but do not comprise HPV type 58 to which Chinese women and Asian women are generally susceptible.

Therefore, HPV vaccines which are safe and effective for women in developing countries such as in China and Asia, in particular, those directed to high-risk type such as HPV 16, 18 and 58, are effective means for effectively preventing cervical cancer and improving the health condition of women, in particular the health condition of Chinese and Asian women.

HPV L1 protein, with a molecular weight of 55-60 kDa, is the major capsid protein of the human papillomavirus and the main target protein of the HPV vaccine. HPV L1 protein expressed in many expression systems can form Virus-Like Particles (VLPs) which resemble native HPV particles morphologically, without the assistance of the L2 protein. The VLPs, consisting of 72 pentamers of the L1 proteins, exhibit icosahedral symmetry. Since the VLPs retain the native epitopes of the viral particles, they are highly immunogenic and can induce the generation of neutralization antibodies against homologous HPV (Kirnbauer, R., F. Booy, et al. 1992 Proc Natl Acad Sci USA 89(24): 12180-4). Furthermore, the VLPs are safe and have no potential cancergenic risk as they contain no viral nucleic acids. Therefore, VLP vaccines have become the primary candidate for HPV vaccines.

The key for development of HPV VLP vaccines lies in efficient production of VLP samples in large-scale. Currently, the most common expression systems used for VLP are divided into eukaryotic expression systems and prokaryotic expression systems.

The commonly used eukaryotic expression systems comprise poxvirus, insect baculovirus and yeast expression systems. HPV L1 protein expressed in eukaryotic expression systems shows little conformational difference from that of the native virus, and can self-assemble into VLPs. Thus, purified VLPs can be easily obtained after simple gradient density centrifugation. It brings a lot of convenience to the purification work. However, due to the high culture costs and low expression level of eukaryotic expression systems, it is quite difficult to product industrially on a large-scale. The HPV vaccine Gardasil®, which came into the market recently, is more expensive than others due to low expression level and high production cost of the *Saccharomyces cerevisiae* expression system employed in its manufacture, and therefore, its general application is limited.

The expression of HPV L1 protein in a prokaryotic expression system such as *E. coli* expression system has been previously reported. The expression of HPV 16 L1 protein by employing *E. coli* has been reported (Banks, L., G. Matlashewski, et al. (1987). J Gen Virol 68 (Pt 12): 3081-9). However, most HPV L1 proteins expressed in *E. coli* lose their native conformation and cannot induce protective antibodies against HPV. Alternatively, although HPV VLPs can be obtained from the proteins by steps such as purification from inclusion bodies and renaturation (Kelsall, S. R. and J. K. Kulski (1995). J Virol Methods 53(1): 75-90), it is difficult to apply this method to large-scale production, as the proteins are largely lost during the renaturation process and the yield is low. Although HPV L1 protein may be expressed in a soluble form with a correct conformation in *E. coli* and be dissolved in the supernatants of *E. coli* lysate, the expression level is low. Moreover, since there are large number and amounts of impure proteins, it is difficult to isolate the proteins of interest from them. Although it is also reported that the expression level of L1 protein can be increased in the supernatants by means of GST fusion expression and the purification of the protein of interest is facilitated (Li, M., T. P. Cripe, et al. (1997), J Virol 71(4): 2988-95), it still cannot be applied to larger-scale production because expensive enzymes are required to cleave the fusion protein.

Therefore, the obtainment of a HPV L1 protein capable of inducing the generation of protective antibodies against HPV, and a virus-like particle consisting of the same, at low cost, are still urgent in the art, in order to make the large-scale industrial production of vaccines for cervical cancer possible.

DESCRIPTION OF THE INVENTION

The invention is at least partially based on the inventors' surprised discovery: a truncated HPV58 L1 protein capable of inducing the generation of neutralization antibodies against HPV58 can be expressed in an *E. coli* expression system on a large scale, wherein the truncated HPV58 L1 protein can be produced with a high yield, and the purity of the purified protein reaches at least 50% or higher (such as 60%, 70%, 80%, 90%, 95%, 96%, 97%, 98%, and 99%). Moreover, further treatment of the purified protein results in the obtainment of VLPs capable of inducing the generation of protective antibodies against HPV58.

Therefore, in one aspect, the invention relates to a truncated HPV58 L1 protein or variants thereof, wherein said protein has 5-70 amino acids, for example, 5-60, 15-60, 20-50, 30-45, 35-40 amino acids, such as 5, 15, 27, 35, 40, 60 or 70 amino acids, truncated at its N-terminal.

In one aspect, the invention relates to a truncated HPV58 L1 protein or variants thereof, wherein said protein has 5-70 amino acids, for example, 5-60, 15-60, 20-50, 30-45, 35-40 amino acids, such as 5, 15, 27, 35, 40, 60 or 70 amino acids, truncated at its N-terminal, as compared with wild type HPV58 L1 protein.

In a preferred embodiment, the truncated HPV58 L1 protein has 5-70 amino acids, such as 5, 15, 27, 35, 40, 60 or 70 amino acids, truncated at its N-terminal, as compared with wild type HPV58 L1 protein. In another preferred embodiment, the truncated HPV58 L1 protein has 35 amino acids truncated at its N-terminal, as compared with wild type HPV58 L1 protein.

In another preferred embodiment, the truncated HPV58 L1 protein (cited hereafter as the truncated protein) has an amino acid sequence as set forth in SEQ ID NO:1, SEQ ID NO:2, SEQ ID NO:3, SEQ ID NO:4, SEQ ID NO:5, SEQ ID NO:6, or SEQ ID NO:7. In another preferred embodiment, the truncated protein has an amino acid sequence as set forth in SEQ ID NO:1.

In another aspect, the invention relates to a polynucleotide encoding the truncated protein or variants thereof according to the invention, and a vector containing the polynucleotide.

Vectors for inserting a polynucleotide of interest are well known in the art, including, but not limited to clone vectors and expression vectors. In one embodiment, the vectors are, for example, plasmids, phages, cosmids, etc.

In another aspect, the invention also relates to a host cell comprising the polynucleotide or vector. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV58 virus-like particle, comprising or consisting of the truncated protein or variants thereof according to the invention.

In one preferred embodiment, the HPV58 virus-like particle according to invention comprises or is consisted of or formed from the truncated HPV58 L1 protein having 5-70 amino acids, for example, 5-60, 15-60, 20-50, 30-45, 35-40 amino acids, such as 5, 15, 27, 35, 40, 60 or 70 amino acids, truncated at its N-terminal, as compared with wild type HPV58 L1 protein. In a particularly preferred embodiment, the HPV58 virus-like particle according to invention comprises or is consisted of or formed from the truncated HPV58 L1 protein having a sequence as set forth in SEQ ID NO:1, SEQ ID NO:2, SEQ ID NO:3, SEQ ID NO:4, SEQ ID NO:5, SEQ ID NO:6, or SEQ ID NO:7.

In another aspect, the invention also relates to a composition comprising said truncated protein or variants thereof, or said polynucleotide or vector or host cell or HPV58 virus-like particle. In one preferred embodiment, the composition comprises the truncated protein or variants thereof according to the invention. In another preferred embodiment, the composition comprises the HPV58 virus-like particle according to the invention.

In another aspect, the invention also relates to a pharmaceutical composition or vaccine comprising the HPV58 virus-like particle according to invention, and optionally pharmaceutically acceptable carriers and/or excipients. The pharmaceutical composition or vaccine according to the invention is useful for preventing HPV (particularly HPV58) infection, and a disease caused by HPV (particularly HPV58) infection, such as cervical cancer.

In one preferred embodiment, the HPV58 virus-like particle is present at an amount effective for preventing HPV infection or cervical cancer. In another preferred embodiment, the pharmaceutical composition or vaccine according to the invention further comprises at least one virus-like particle selected from the group consisting of HPV6 L1 protein virus-like particle, HPV11 L1 protein virus-like particle, HPV16 L1 protein virus-like particle, HPV18 L1 protein virus-like particle, HPV31 L1 protein virus-like particle, HPV33 L1 protein virus-like particle, HPV45 L1 protein virus-like particle, and HPV52 L1 protein virus-like particle; preferably these virus-like particles are independently present at an amount effective for preventing cervical cancer or infection by the corresponding HPV subtype.

The pharmaceutical composition or vaccine according to the invention may be administrated by methods well known in the art, for example, but not limited to, orally or by injection. In the invention, the particularly preferred administration route is injection.

In one preferred embodiment, the pharmaceutical composition or vaccine according to the invention is administrated in a form of a unit dosage. For example, but not for limiting the invention, each unit dosage contains 5 μg-80 μg, preferably 20 μg-40 μg HPV58 virus-like particle.

In another aspect, the invention relates to a method for obtaining the truncated protein according to the invention, comprising expressing the truncated protein according to the invention with an *E. coli* expression system, and carrying out a purification process on the lysis supernatant containing the truncated protein.

In a preferred embodiment, the method for obtaining the truncated protein according to the invention comprises, a) expressing the truncated protein in *E. coli*;

b) disrupting the *E. coli*, which has expressed the truncated protein, in a solution at a salt concentration of 100 mM to 600 mM, and isolating the supernatant;

c) decreasing the salt concentration of the supernatant of b) to 100 mM or less, by using water or a solution at a low salt concentration, lowest to 0, and collecting a precipitate;

d) re-dissolving the precipitate of c) in a solution at a salt concentration of 150 mM to 2500 mM, and adding a reductant to the solution, and then isolating the resultant solution, wherein the resultant solution contains the truncated HPV58 L1 protein with a purity of at least 50%.

In one embodiment of the invention, the salt concentration in b) is from 200 mM to 500 mM.

More generally, the invention also relates to a method for obtaining HPV L1 protein, such as the truncated protein according to the invention, comprising, a) expressing HPV L1 gene encoding HPV L1 protein in *E. coli*;

b) disrupting the *E. coli*, which has expressed the HPV L1 protein, in a solution at a salt concentration of 100 mM to 600 mM, and isolating the supernatant;

c) decreasing the salt concentration of the supernatant of b) to 100 mM or less, by using water or a solution at a low salt concentration, lowest to 0, and collecting a precipitate;

d) re-dissolving the precipitate of c) in a solution at a salt concentration of 150 mM to 2500 mM, and adding a reductant to the solution, and then isolating the resultant solution, wherein the resultant solution contains the HPV L1 protein with a purity of at least 50%.

The invention also relates to a method for obtaining the HPV58 virus-like particle according to invention, on the basis of the obtainment of the truncated protein of the invention as described above, comprising the steps of:

e) further purifying the truncated HPV58 L1 protein according to the invention with a purity of at least 50% by a chromatography; and f) removing the reductant from the truncated protein obtained in e).

The invention also relates to a method for preparing a vaccine, comprising blending the HPV58 virus-like particle according to the invention, and optionally, one or more virus-like particles selected from the group consisting of virus-like particles of HPV types 6, 11, 16, 18, 31, 33, 45 and 52, with pharmaceutically acceptable carriers and/or excipients. As described above, the vaccine obtained is useful for preventing HPV (particularly HPV58) infection, and a disease caused by HPV (particularly HPV58) infection, such as cervical cancer.

In another aspect, the invention relates to a method for preventing HPV infection or a disease caused by HPV infection, comprising administrating to a subject a prophylactically effective amount of the HPV58 virus-like particle or pharmaceutical composition or vaccine according to the invention. In one preferred embodiment, the HPV infection is HPV58 infection. In another preferred embodiment, the disease caused by HPV infection includes, but is not limited to cervical cancer. In another preferred embodiment, the subject is mammalian, such as human.

In another aspect, the invention also relates to the use of the truncated protein or variants thereof or the HPV58 virus-like particle according to invention in the preparation of a pharmaceutical composition or vaccine for preventing HPV infection or a disease caused by HPV infection. In one preferred embodiment, the HPV infection is HPV58 infection. In another preferred embodiment, the disease caused by HPV infection includes, but is not limited to cervical cancer.

In another aspect, the invention also relates to the truncated protein or variants thereof or the HPV58 virus-like particle according to invention, for use in the prevention of HPV infection or a disease caused by HPV infection. In one preferred embodiment, the HPV infection is HPV58 infection. In another preferred embodiment, the disease caused by HPV infection includes, but is not limited to cervical cancer.

Definitions of the Term in the Present Invention

In the invention, unless otherwise specified, the scientific and technical terms used herein have the meanings as generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a protein having X amino acids truncated at its N-terminal" refers to a protein resulted from substituting the amino acid residues from positions 1 to X at the N-terminal of the protein with methionine residue encoded by an initiator codon (for initiating protein translation). For example, a HPV58 L1 protein having 35 amino acids truncated at its N-terminal refers to a protein resulted from substituting the amino acid residues from positions 1 to 35 at the N-terminal of wild type HPV58 L1 protein with methionine residue encoded by an initiator codon.

According to the invention, the term "variant" refers to a protein, whose amino acid sequence is different from the truncated HPV58 L1 protein according to the invention (for example, the protein as set forth in SEQ ID NO:1 or SEQ ID NO:2) by one or more (for example, 1-10, or 1-5 or 1-3) amino acids (such as conservative amino acid substitutions), or which has an identity of at least 60%, 80%, 85%, 90%, 95%, 96%, 97%, 98%, or 99% to the truncated HPV58 L1 protein according to the invention (for example, the protein as set forth in SEQ ID NO:1 or SEQ ID NO:2), and which retains the essential characteristics of the truncated protein. The term "essential characteristics" may be one or more of the following characteristics: capable of inducing the generation of neutralization antibodies against HPV58; capable of being expressed in *E. coli* in a soluble manner; capable of obtaining purified protein with a high yield by the expression and purification methods as involved in the invention.

According to the invention, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used in the invention, the term "conservative substitution" refers to amino acid substitutions which would not negatively affect or change the biological activity of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue similar to the corresponding amino acid residue physically or functionally (such as, having similar size, shape, charges, chemical properties including the capability of forming covalent bond or hydrogen bond, etc.). The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

According to the invention, the term "*E. coli* expression system" refers to an expression system consisting of *E. coli* (strain) and a vector, wherein the *E. coli* (strain) includes, but are not limited to: GI698, ER2566, BL21 (DE3), B834 (DE3), BLR (DE3), etc., which are available on the market.

According to the invention, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, and transfection into the host cell. Vectors are well known by a person skilled in the art, including, but not limited to plasmids, phages, cosmids and the like.

According to the invention, the term "a truncated HPV58 L1 protein" refers to the protein with one or more amino acids deleted at the N- and/or C-terminal of wild-type HPV58 L1 protein, wherein the example of the wild-type HPV58 L1 protein includes, but is not limited to, the full-length L1 proteins such as ACJ13480, ACX32376.1 or ACK37663.1 in NCBI database.

According to the invention, the term "a gene fragment of a truncated HPV58 L1 protein" refers to the gene fragments with the nucleotide(s) encoding one or more amino acids deleted at 5' or 3' terminal of the wild-type HPV58 L1 gene, wherein the full-length gene sequence of the wild-type HPV58 L1 gene includes, but is not limited to, the following sequences: AY101598.2, D90400.1, FJ407208.1, FJ615305.1 and FN178626.1 in NCBI database.

According to the invention, the term "pharmaceutically acceptable carriers and/or excipients" refers to carriers and/or excipients that are pharmacologically and/or physiologically compatible with subjects and active ingredients, and are well known in the art (see, for example, Remington's Pharmaceutical Sciences. Edited by Gennaro A R, 19th ed. Pennsylvania: Mack Publishing Company, 1995), including, but not limited to pH adjusting agents, surfactants, adjuvants, and ionic strength enhancers. For example, pH adjusting agents include, but are not limited to, phosphate buffers; surfactants include, but are not limited to: anion surfactants, cation surfactants, or non-ionic surfactants (for example, Tween-80); adjuvants include, but are not limited to, aluminum adjuvants (for example, aluminum hydroxide) and Freund's adjuvants (for example, Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (e.g. cation-exchange chromatography), hydrophobic interaction chromatography, absorbent chromatography (e.g. hydroxyapatite chromatography), gel filtration chromatography (gel exclusion chromatography), and affinity chromatography.

According to the invention, the truncated HPV58 L1 proteins according to the invention may be obtained preferably by the following steps:

disrupting *E. coli*, which expresses a truncated HPV58 L1 protein, in a buffer at a salt concentration of 100-600 mM, preferably 200-500 mM, and centrifuging the disrupted solution to obtain a supernatant;

precipitating the truncated HPV58 L1 protein from the supernatant by decreasing the salt concentration of the resultant supernatant to 100 mM-0 mM with water or a low-salt solution (generally, with a salt concentration lower than the one of the buffer for disrupting);

re-dissolving the precipitate in a solution containing a reductant and having a salt concentration of 150-2500 mM, preferably greater than 200 mM, resulting in a solution comprising the truncated HPV58 L1 proteins with a purity of at least 50%, preferably at least 70%, more preferably at least 80%.

The buffers used in the methods of the invention are well known in the art, including, but not limited to Tris buffers, phosphate buffers, HEPES buffers, MOPS buffers, etc.

According to the invention, the disrupting of the host cell can be accomplished by methods well known by a person skilled in the art, including, but not limited to homogenizer disrupting, ultrasonic treatment, grinding, high pressure extrusion, lysozyme treatment, etc.

The salts used in the methods of the invention include, but are not limited to: one or more of acidic salts, basic salts, neutral salts, for example, alkali metal salts, alkaline-earth metal salts, ammonium salts, hydrochlorides, sulfates, bicarbonates, phosphate salts or biphosphates, especially NaCl, KCl, $NH_4Cl$, $(NH_4)_2SO_4$. NaCl is particularly preferred. The reductant used in the methods of the invention includes, but is not limited to, DTT and 2-mercaptoethanol, at an amount including, but not limited to, 10-100 mM.

According to the invention, the HPV58 VLPs according to the invention may be produced by the following steps: further purifying the truncated HPV58 L1 protein with a purity of at least 50% as described above by e.g. a chromatography, and thereby obtaining a purified truncated protein solution; and removing the reductant from the solution to obtain the HPV58 VLPs. Methods for removing the reductant are known in the art, including, but not limited to, dialysis, ultrafiltration, and chromatography.

Beneficial Effect

Presently, the expression systems useful for preparing HPV VLPs include eukaryotic and prokaryotic expression systems.

HPV L1 proteins expressed in eukaryotic expression systems show little conformational difference from that of the native virus, and can self-assemble into VLPs. In most cases, VLPs with a correct conformation can be obtained by simple purification. Nevertheless, eukaryotic expression systems, such as the baculovirus and yeast expression systems, are difficult to be applied to large-scale industrial production due to shortcomings such as low expression levels and high culturing costs.

Prokaryotic expression systems, such as *E. coli* systems, have the advantages of high expression levels and low culturing costs. However, when expressed in *E. coli* system, HPV L1 proteins usually lose their native conformations and are expressed in a form of inclusion bodies in the precipitant. Currently, renaturation of the protein from inclusion bodies is still a challenge worldwide. Due to the difficulty and inefficiency of renaturation, this method is limited to small-scale lab research and cannot be applied to the large-scale obtainment of VLPs with a correct conformation from the inclusive bodies. Although HPV L1 protein may be expressed in a soluble form with a correct conformation in *E. coli*, their expression levels are low. Moreover, it is quite difficult to purify the HPV L1 proteins from the numerous soluble proteins in the *E. coli* lysate supernatant. Generally, the purification is carried out by means such as fusion expression and affinity chromatography which are not feasible for industrial-scale processes due to expensive enzymes employed therein.

The N-truncated HPV58 L1 protein and the method for preparing the same, as provided in the invention, effectively solve the problem. Firstly, *E. coli* expression systems are used in the invention to express the N-truncated HPV58 L1 protein, which ensures a high expression level. Secondly, the truncated protein is selectively precipitated from the *E. coli* lysate supernatant under mild conditions. The truncated protein is then redissolved in a salt buffer to significantly improve its purity while still retaining its correct conformation. The truncated protein solution thus obtained can be further purified directly by chromatography such as ion-exchange and hydrophobic exchange chromatography so as to obtain the protein of interest with a high purity (such as a purity up to 80%). Further, the purified, truncated protein obtained from these steps, can self-assemble into VLP with good immunogenicity and the ability to induce neutralization antibodies of a high titer against HPV58, which is a good vaccine for preventing HPV58 infection in human.

Therefore, the invention has the following advantages. The truncated protein of the invention can be expressed in *E. coli* expression systems on a large scale whilst retaining the antigenicity, immunogenicity, and particle self-assembly ability of the full-length HPV58 L1 protein. Expensive enzymes are not required in the preparation methods used in the invention, i.e. the cost is low. Furthermore, since the truncated protein is not subjected to the intensive procedures of denaturation and renaturation during purification, the loss of the protein is low and the yield is high. The VLPs formed from the truncated protein can induce the generation of protective antibodies against HPV at a high titer and can be applied to the preparation of vaccines. Thus, the truncated protein of the invention and the preparation method thereof can be applied to large-scale industrial production, and makes the large-scale industrial production of vaccines for cervical cancer possible.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF DRAWINGS

FIG. 7A, HPV58N5C-L1 VLPs; FIG. 7B, HPV58N15C-L1 VLPs; FIG. 7C, HPV58N27C-L1 VLPs; FIG. 7D, HPV58N40C-L1 VLPs; FIG. 7E, HPV58N60C-L1 VLPs; FIG. 7F, HPV58N70C-L1 VLPs. The results showed that a large number of VLPs with a radius of about 25 nm were observed in visual field in FIGS. 7A-7F, wherein the particle size was consistent with the theoretic size and the particles were homogenous.

FIG. 8A, HPV58N5C-L1 VLPs; FIG. 8B, HPV58N15C-L1 VLPs; FIG. 8C, HPV58N27C-L1 VLPs; FIG. 8D, HPV58N40C-L1 VLPs; FIG. 8E, HPV58N60C-L1 VLPs; FIG. 8F, HPV58N70C-L1 VLPs. The results showed that HPV58N5C-L1, HPV58N15C-L1, HPV58N27C-L1, HPV58N40C-L1, HPV58N60C-L1, and HPV58N70C-L1 VLPs had a hydrodynamic radius of about 25 nm and a particle assembly rate of 100%.

SEQUENCE INFORMATION

Figure 1:
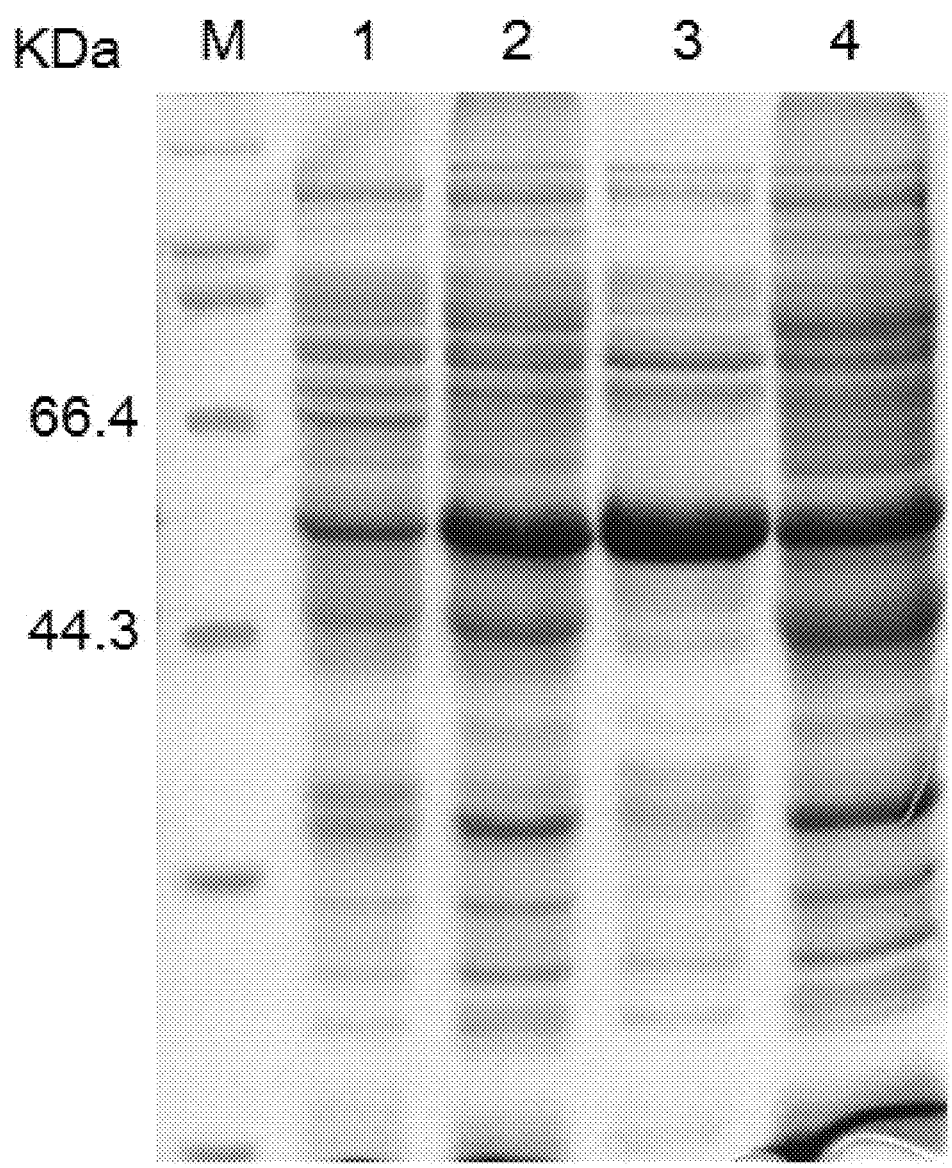
FIG. 1 shows the SDS-PAGE result of the HPV58N35C-L1 protein obtained during different steps of Example 2 of the invention. Lane M: protein molecular weight marker; Lane 1: supernatant of disrupted bacteria (i.e. the supernatant obtained by centrifuging the disrupted bacteria); Lane 2: precipitate product free of salts (i.e. the precipitate obtained by centrifugation after dialysis); Lane 3: re-dissolved supernatant (i.e. the supernatant obtained by centrifuging the solution resulted from re-dissolving the precipitate product free of salts); Lane 4: precipitant obtained after re-dissolution (i.e. the precipitate obtained by centrifuging the solution resulted from re-dissolving the precipitate product free of salts). The result showed that the purity of HPV58N35C-L1 protein was increased from about 10% (see Lane 1) to about 70% (see Lane 3) after the steps of precipitation and re-dissolution.

The information on the sequences involved in the invention is provided in the following Table 1.

TABLE 1

Depiction of sequences

| SEQ ID NO | depiction |
| --- | --- |
| 1 | a HPV58 L1 protein having 35 amino acids truncated at its N-terminal, HPV58N35C-L1 |
| 2 | a HPV58 L1 protein having 5 amino acids truncated at its N-terminal, HPV58N5C-L1 |
| 3 | a HPV58 L1 protein having 15 amino acids truncated at its N-terminal, HPV58N15C-L1 |
| 4 | a HPV58 L1 protein having 27 amino acids truncated at its N-terminal, HPV58N27C-L1 |
| 5 | a HPV58 L1 protein having 40 amino acids truncated at its N-terminal, HPV58N40C-L1 |
| 6 | a HPV58 L1 protein having 60 amino acids truncated at its N-terminal, HPV58N60C-L1 |

TABLE 1 -continued

Depiction of sequences

| SEQ ID NO: | depiction |
|---|---|
| 7 | a HPV58 L1 protein having 70 amino acids truncated at its N-terminal, HPV58N70C-L1 |
| 8 | HPV58 L1 gene sequence (1575 bp) |
| 9 | a DNA sequence encoding SEQ ID NO: 1 |
| 10 | a DNA sequence encoding SEQ ID NO: 2 |
| 11 | a DNA sequence encoding SEQ ID NO: 3 |
| 12 | a DNA sequence encoding SEQ ID NO: 4 |
| 13 | a DNA sequence encoding SEQ ID NO: 5 |
| 14 | a DNA sequence encoding SEQ ID NO: 6 |
| 15 | a DNA sequence encoding SEQ ID NO: 7 |
| 16 | primer |
| 17 | primer |

Sequence 1 (SEQ ID NO: 1):
MTVYLPPVPVSKVVSTDEYVSRTSIYYYAGSSRLLAVGNPYFSIKSPNNNKKVLVPKVSGLQYRVFRVRLP
DPNKFGFPDTSFYNPDTQRLVWACVGLEIGRGQPLGVGVSGHPYLNKFDDTETSNRYPAQPGSDNRECLSM
DYKQTQLCLIGCKPPTGEHWGKGVACNNNAAATDCPPLELFNSIIEDGDMVDTGFGCMDFGTLQANKSDVP
IDICNSTCKYPDYLKMASEPYGDSLFFFLRREQMFVRHFFNRAGKLGEAVPDDLYIKGSGNTAVIQSSAFF
PTPSGSIVTSESQLFNKPYWLQRAQGHNNGICWGNQLFVTVVDTTRSTNMTLCTEVTKEGTYKNDNFKEYV
RHVEEYDLQFVFQLCKITLTAEIMTYIHTMDSNILEDWQFGLTPPPSASLQDTYRFVTSQAITCQKTAPPK
EKEDPLNKYTFWEVNLKEKFSADLDQFPLGRKFLLQSGLKAKPRLKRSAPTTRAPSTKRKKVKK Sequence 2 (SEQ ID NO: 2):
MCCTLAILFCVADVNVFHIFLQMSVWRPSEATVYLPPVPVSKVVSTDEYVSRTSIYYYAGSSRLLAVGNPY
FSIKSPNNNKKVLVPKVSGLQYRVFRVRLPDPNKFGFPDTSFYNPDTQRLVWACVGLEIGRGQPLGVGVSG
HPYLNKFDDTETSNRYPAQPGSDNRECLSMDYKQTQLCLIGCKPPTGEHWGKGVACNNNAAATDCPPLELF
NSIIEDGDMVDTGFGCMDFGTLQANKSDVPIDICNSTCKYPDYLKMASEPYGDSLFFFLRREQMFVRHFFN
RAGKLGEAVPDDLYIKGSGNTAVIQSSAFFPTPSGSIVTSESQLFNKPYWLQRAQGHNNGICWGNQLFVTV
VDTTRSTNMTLCTEVTKEGTYKNDNFKEYVRHVEEYDLQFVFQLCKITLTAEIMTYIHTMDSNILEDWQFG
LTPPPSASLQDTYRFVTSQAITCQKTAPPKEKEDPLNKYTFWEVNLKEKFSADLDQFPLGRKFLLQSGLKA
KPRLKRSAPTTRAPSTKRKKVKK Sequence 3 (SEQ ID NO: 3):
MADVNVFHIFLQMSVWRPSEATVYLPPVPVSKVVSTDEYVSRTSIYYYAGSSRLLAVGNPYFSIKSPNNNK
KVLVPKVSGLQYRVFRVRLPDPNKFGFPDTSFYNPDTQRLVWACVGLEIGRGQPLGVGVSGHPYLNKFDDT
ETSNRYPAQPGSDNRECLSMDYKQTQLCLIGCKPPTGEHWGKGVACNNNAAATDCPPLELFNSIIEDGDMV
DTGFGCMDFGTLQANKSDVPIDICNSTCKYPDYLKMASEPYGDSLFFFLRREQMFVRHFFNRAGKLGEAVP
DDLYIKGSGNTAVIQSSAFFPTPSGSIVTSESQLFNKPYWLQRAQGHNNGICWGNQLFVTVVDTTRSTNMT
LCTEVTKEGTYKNDNFKEYVRHVEEYDLQFVFQLCKITLTAEIMTYIHTMDSNILEDWQFGLTPPPSASLQ
DTYRFVTSQAITCQKTAPPKEKEDPLNKYTFWEVNLKEKFSADLDQFPLGRKFLLQSGLKAKPRLKRSAPT
TRAPSTKRKKVKK Sequence 4 (SEQ ID NO: 4):
MSVWRPSEATVYLPPVPVSKVVSTDEYVSRTSIYYYAGSSRLLAVGNPYFSIKSPNNNKKVLVPKVSGLQY
RVFRVRLPDPNKFGFPDTSFYNPDTQRLVWACVGLEIGRGQPLGVGVSGHPYLNKFDDTETSNRYPAQPGS
DNRECLSMDYKQTQLCLIGCKPPTGEHWGKGVACNNNAAATDCPPLELFNSIIEDGDMVDTGFGCMDFGTL
QANKSDVPIDICNSTCKYPDYLKMASEPYGDSLFFFLRREQMFVRHFFNRAGKLGEAVPDDLYIKGSGNTA
VIQSSAFFPTPSGSIVTSESQLFNKPYWLQRAQGHNNGICWGNQLFVTVVDTTRSTNMTLCTEVTKEGTYK
NDNFKEYVRHVEEYDLQFVFQLCKITLTAEIMTYIHTMDSNILEDWQFGLTPPPSASLQDTYRFVTSQAIT
CQKTAPPKEKEDPLNKYTFWEVNLKEKFSADLDQFPLGRKFLLQSGLKAKPRLKRSAPTTRAPSTKRKKVK
K Sequence 5 (SEQ ID NO: 5):
MPVPVSKVVSTDEYVSRTSIYYYAGSSRLLAVGNPYFSIKSPNNNKKVLVPKVSGLQYRVFRVRLPDPNKF
GFPDTSFYNPDTQRLVWACVGLEIGRGQPLGVGVSGHPYLNKFDDTETSNRYPAQPGSDNRECLSMDYKQT
QLCLIGCKPPTGEHWGKGVACNNNAAATDCPPLELFNSIIEDGDMVDTGFGCMDFGTLQANKSDVPIDICN
STCKYPDYLKMASEPYGDSLFFFLRREQMFVRHFFNRAGKLGEAVPDDLYIKGSGNTAVIQSSAFFPTPSG
SIVTSESQLFNKPYWLQRAQGHNNGICWGNQLFVTVVDTTRSTNMTLCTEVTKEGTYKNDNFKEYVRHVEE
YDLQFVFQLCKITLTAEIMTYIHTMDSNILEDWQFGLTPPPSASLQDTYRFVTSQAITCQKTAPPKEKEDP
LNKYTFWEVNLKEKFSADLDQFPLGRKFLLQSGLKAKPRLKRSAPTTRAPSTKRKKVKK Sequence 6 (SEQ ID NO: 6):
MYYAGSSRLLAVGNPYFSIKSPNNNKKVLVPKVSGLQYRVFRVRLPDPNKFGFPDTSFYNPDTQRLVWACV
GLEIGRGQPLGVGVSGHPYLNKFDDTETSNRYPAQPGSDNRECLSMDYKQTQLCLIGCKPPTGEHWGKGVA
CNNNAAATDCPPLELFNSIIEDGDMVDTGFGCMDFGTLQANKSDVPIDICNSTCKYPDYLKMASEPYGDSL TABLE 1 -continued Depiction of sequences SEQ ID NO:depiction FFFLRREQMFVRHFFNRAGKLGEAVPDDLYIKGSGNTAVIQSSAFFPTPSGSIVTSESQLFNKPYWLQRAQ
GHNNGICWGNQLFVTVVDTTRSTNMTLCTEVTKEGTYKNDNFKEYVRHVEEYDLQFVFQLCKITLTAEIMT
YIHTMDSNILEDWQFGLTPPPSASLQDTYRFVTSQAITCQKTAPPKEKEDPLNKYTFWEVNLKEKFSADLD
QFPLGRKFLLQSGLKAKPRLKRSAPTTRAPSTKRKKVKK Sequence 7 (SEQ ID NO: 7):
MVGNPYFSIKSPNNNKKVLVPKVSGLQYRVFRVRLPDPNKFGFPDTSFYNPDTQRLVWACVGLEIGRGQPL
GVGVSGHPYLNKFDDTETSNRYPAQPGSDNRECLSMDYKQTQLCLIGCKPPTGEHWGKGVACNNNAAATDC
PPLELFNSIIEDGDMVDTGFGCMDFGTLQANKSDVPIDICNSTCKYPDYLKMASEPYGDSLFFFLRREQMF
VRHFFNRAGKLGEAVPDDLYIKGSGNTAVIQSSAFFPTPSGSIVTSESQLFNKPYWLQRAQGHNNGICWGN
QLFVTVVDTTRSTNMTLCTEVTKEGTYKNDNFKEYVRHVEEYDLQFVFQLCKITLTAEIMTYIHTMDSNIL
EDWQFGLTPPPSASLQDTYRFVTSQAITCQKTAPPKEKEDPLNKYTFWEVNLKEKFSADLDQFPLGRKFLL
QSGLKAKPRLKRSAPTTRAPSTKRKKVKK Sequence 8 (SEQ ID NO: 8):
ATGGTGCTGATCCTGTGCTGCACCCTGGCCATCCTGTTCTGCGTGGCCGACGTGAACGTGTTCCACATCTT
CCTGCAGATGAGCGTGTGGAGGCCCAGCGAGGCCACCGTGTACCTGCCCCCCGTGCCCGTGAGCAAGGTGG
TGAGCACCGACGAGTACGTGAGCAGGACCAGCATCTACTACTACGCCGGCAGCAGCAGGCTGCTGGCCGTG
GGCAACCCCTACTTCAGCATCAAGAGCCCCAACAACAACAAGAAGGTGCTGGTGCCCAAGGTGAGCGGCCT
GCAGTACAGGGTGTTCAGGGTGAGGCTGCCCGACCCCAACAAGTTCGGCTTCCCCGACACCAGCTTCTACA
ACCCCGACACCCAGAGGCTGGTGTGGGCCTGCGTGGGCCTGGAGATCGGCAGGGGCCAGCCCCTGGGCGTG
GGCGTGAGCGGCCACCCCTACCTGAACAAGTTCGACGACACCGAGACCAGCAACAGGTACCCCGCCCAGCC
CGGCAGCGACAACAGGGAGTGCCTGAGCATGGACTACAAGCAGACCCAGCTGTGCCTGATCGGCTGCAAGC
CCCCCACCGGCGAGCACTGGGGCAAGGGCGTGGCCTGCAACAACAACGCCGCCGCCACCGACTGCCCCCCC
CTGGAGCTGTTCAACAGCATCATCGAGGACGGCGACATGGTGGACACCGGCTTCGGCTGCATGGACTTCGG
CACCCTGCAGGCCAACAAGAGCGACGTGCCCATCGACATCTGCAACAGCACCTGCAAGTACCCCGACTACC
TGAAGATGGCCAGCGAGCCCTACGGCGACAGCCTGTTCTTCTTCCTGAGGAGGGAGCAGATGTTCGTGAGG
CACTTCTTCAACAGGGCCGGCAAGCTGGGCGAGGCCGTGCCCGACGACCTGTACATCAAGGGCAGCGGCAA
CACCGCCGTGATCCAGAGCAGCGCCTTCTTCCCCACCCCCAGCGGCAGCATCGTGACCAGCGAGAGCCAGC
TGTTCAACAAGCCCTACTGGCTGCAGAGGGCCCAGGGCCACAACAACGGCATCTGCTGGGGCAACCAGCTG
TTCGTGACCGTGGTGGACACCACCAGGAGCACCAACATGACCCTGTGCACCGAGGTGACCAAGGAGGGCAC
CTACAAGAACGACAACTTCAAGGAGTACGTGAGGCACGTGGAGGAGTACGACCTGCAGTTCGTGTTCCAGC
TGTGCAAGATCACCCTGACCGCCGAGATCATGACCTACATCCACACCATGGACAGCAACATCCTGGAGGAC
TGGCAGTTCGGCCTGACCCCCCCCCCCAGCGCCAGCCTGCAGGACACCTACAGGTTCGTGACCAGCCAGGC
CATCACCTGCCAGAAGACCGCCCCCCCCAAGGAGAAGGAGGACCCCCTGAACAAGTACACCTTCTGGGAGG
TGAACCTGAAGGAGAAGTTCAGCGCCGACCTGGACCAGTTCCCCCTGGGCAGGAAGTTCCTGCTGCAGAGC
GGCCTGAAGGCCAAGCCCAGGCTGAAGAGGAGCGCCCCCACCACCAGGGCCCCCAGCACCAAGAGGAAGAA
GGTGAAGAAGTGA Sequence 9 (SEQ ID NO: 9):
ATGACCGTGTACCTGCCCCCCGTGCCCGTGAGCAAGGTGGTGAGCACCGACGAGTACGTGAGCAGGACCAG
CATCTACTACTACGCCGGCAGCAGCAGGCTGCTGGCCGTGGGCAACCCCTACTTCAGCATCAAGAGCCCCA
ACAACAACAAGAAGGTGCTGGTGCCCAAGGTGAGCGGCCTGCAGTACAGGGTGTTCAGGGTGAGGCTGCCC
GACCCCAACAAGTTCGGCTTCCCCGACACCAGCTTCTACAACCCCGACACCCAGAGGCTGGTGTGGGCCTG
CGTGGGCCTGGAGATCGGCAGGGGCCAGCCCCTGGGCGTGGGCGTGAGCGGCCACCCCTACCTGAACAAGT
TCGACGACACCGAGACCAGCAACAGGTACCCCGCCCAGCCCGGCAGCGACAACAGGGAGTGCCTGAGCATG
GACTACAAGCAGACCCAGCTGTGCCTGATCGGCTGCAAGCCCCCCACCGGCGAGCACTGGGGCAAGGGCGT
GGCCTGCAACAACAACGCCGCCGCCACCGACTGCCCCCCCCTGGAGCTGTTCAACAGCATCATCGAGGACG
GCGACATGGTGGACACCGGCTTCGGCTGCATGGACTTCGGCACCCTGCAGGCCAACAAGAGCGACGTGCCC
ATCGACATCTGCAACAGCACCTGCAAGTACCCCGACTACCTGAAGATGGCCAGCGAGCCCTACGGCGACAG
CCTGTTCTTCTTCCTGAGGAGGGAGCAGATGTTCGTGAGGCACTTCTTCAACAGGGCCGGCAAGCTGGGCG
AGGCCGTGCCCGACGACCTGTACATCAAGGGCAGCGGCAACACCGCCGTGATCCAGAGCAGCGCCTTCTTC
CCCACCCCCAGCGGCAGCATCGTGACCAGCGAGAGCCAGCTGTTCAACAAGCCCTACTGGCTGCAGAGGGC
CCAGGGCCACAACAACGGCATCTGCTGGGGCAACCAGCTGTTCGTGACCGTGGTGGACACCACCAGGAGCA
CCAACATGACCCTGTGCACCGAGGTGACCAAGGAGGGCACCTACAAGAACGACAACTTCAAGGAGTACGTG
AGGCACGTGGAGGAGTACGACCTGCAGTTCGTGTTCCAGCTGTGCAAGATCACCCTGACCGCCGAGATCAT
GACCTACATCCACACCATGGACAGCAACATCCTGGAGGACTGGCAGTTCGGCCTGACCCCCCCCCCCAGCG
CCAGCCTGCAGGACACCTACAGGTTCGTGACCAGCCAGGCCATCACCTGCCAGAAGACCGCCCCCCCCAAG
GAGAAGGAGGACCCCCTGAACAAGTACACCTTCTGGGAGGTGAACCTGAAGGAGAAGTTCAGCGCCGACCT
GGACCAGTTCCCCCTGGGCAGGAAGTTCCTGCTGCAGAGCGGCCTGAAGGCCAAGCCCAGGCTGAAGAGGA
GCGCCCCCACCACCAGGGCCCCCAGCACCAAGAGGAAGAAGGTGAAGAAGTAA Sequence 10 (SEQ ID NO: 10):
ATGGTGCTGCACCCTGGCCATCCTGTTCTGCGTGGCCGACGTGAACGTGTTCCACATCTTCCTGCAGATGAG
CGTGTGGAGGCCCAGCGAGGCCACCGTGTACCTGCCCCCCGTGCCCGTGAGCAAGGTGGTGAGCACCGACG
AGTACGTGAGCAGGACCAGCATCTACTACTACGCCGGCAGCAGCAGGCTGCTGGCCGTGGGCAACCCCTAC
TTCAGCATCAAGAGCCCCAACAACAACAAGAAGGTGCTGGTGCCCAAGGTGAGCGGCCTGCAGTACAGGGT
GTTCAGGGTGAGGCTGCCCGACCCCAACAAGTTCGGCTTCCCCGACACCAGCTTCTACAACCCCGACACCC
AGAGGCTGGTGTGGGCCTGCGTGGGCCTGGAGATCGGCAGGGGCCAGCCCCTGGGCGTGGGCGTGAGCGGC
CACCCCTACCTGAACAAGTTCGACGACACCGAGACCAGCAACAGGTACCCCGCCCAGCCCGGCAGCGACAA
CAGGGAGTGCCTGAGCATGGACTACAAGCAGACCCAGCTGTGCCTGATCGGCTGCAAGCCCCCCACCGGCG
AGCACTGGGGCAAGGGCGTGGCCTGCAACAACAACGCCGCCGCCACCGACTGCCCCCCCCTGGAGCTGTTC
AACAGCATCATCGAGGACGGCGACATGGTGGACACCGGCTTCGGCTGCATGGACTTCGGCACCCTGCAGGC
CAACAAGAGCGACGTGCCCATCGACATCTGCAACAGCACCTGCAAGTACCCCGACTACCTGAAGATGGCCA
GCGAGCCCTACGGCGACAGCCTGTTCTTCTTCCTGAGGAGGGAGCAGATGTTCGTGAGGCACTTCTTCAAC
AGGGCCGGCAAGCTGGGCGAGGCCGTGCCCGACGACCTGTACATCAAGGGCAGCGGCAACACCGCCGTGAT TABLE 1 -continued Depiction of sequences SEQ ID NO:depiction CCAGAGCAGCGCCTTCTTCCCCACCCCCAGCGGCAGCATCGTGACCAGCGAGAGCCAGCTGTTCAACAAGC
CCTACTGGCTGCAGAGGGCCCAGGGCCACAACAACGGCATCTGCTGGGGCAACCAGCTGTTCGTGACCGTG
GTGGACACCACCAGGAGCACCAACATGACCCTGTGCACCGAGGTGACCAAGGAGGGCACCTACAAGAACGA
CAACTTCAAGGAGTACGTGAGGCACGTGGAGGAGTACGACCTGCAGTTCGTGTTCCAGCTGTGCAAGATCA
CCCTGACCGCCGAGATCATGACCTACATCCACACCATGGACAGCAACATCCTGGAGGACTGGCAGTTCGGC
CTGACCCCCCCCCCCAGCGCCAGCCTGCAGGACACCTACAGGTTCGTGACCAGCCAGGCCATCACCTGCCA
GAAGACCGCCCCCCCCAAGGAGAAGGAGGACCCCCTGAACAAGTACACCTTCTGGGAGGTGAACCTGAAGG
AGAAGTTCAGCGCCGACCTGGACCAGTTCCCCCTGGGCAGGAAGTTCCTGCTGCAGAGCGGCCTGAAGGCC
AAGCCCAGGCTGAAGAGGAGCGCCCCCACCACCAGGGCCCCCAGCACCAAGAGGAAGAAGGTGAAGAAGTG
A Sequence 11 (SEQ ID NO: 11):
ATGGCCGACGTGAACGTGTTCCACATCTTCCTGCAGATGAGCGTGTGGAGGCCCAGCGAGGCCACCGTGTA
CCTGCCCCCCGTGCCCGTGAGCAAGGTGGTGAGCACCGACGAGTACGTGAGCAGGACCAGCATCTACTACT
ACGCCGGCAGCAGCAGGCTGCTGGCCGTGGGCAACCCCTACTTCAGCATCAAGAGCCCCAACAACAACAAG
AAGGTGCTGGTGCCCAAGGTGAGCGGCCTGCAGTACAGGGTGTTCAGGGTGAGGCTGCCCGACCCCAACAA
GTTCGGCTTCCCCGACACCAGCTTCTACAACCCCGACACCCAGAGGCTGGTGTGGGCCTGCGTGGGCCTGG
AGATCGGCAGGGGCCAGCCCCTGGGCGTGGGCGTGAGCGGCCACCCCTACCTGAACAAGTTCGACGACACC
GAGACCAGCAACAGGTACCCCGCCCAGCCCGGCAGCGACAACAGGGAGTGCCTGAGCATGGACTACAAGCA
GACCCAGCTGTGCCTGATCGGCTGCAAGCCCCCCACCGGCGAGCACTGGGGCAAGGGCGTGGCCTGCAACA
ACAACGCCGCCGCCACCGACTGCCCCCCCCTGGAGCTGTTCAACAGCATCATCGAGGACGGCGACATGGTG
GACACCGGCTTCGGCTGCATGGACTTCGGCACCCTGCAGGCCAACAAGAGCGACGTGCCCATCGACATCTG
CAACAGCACCTGCAAGTACCCCGACTACCTGAAGATGGCCAGCGAGCCCTACGGCGACAGCCTGTTCTTCT
TCCTGAGGAGGGAGCAGATGTTCGTGAGGCACTTCTTCAACAGGGCCGGCAAGCTGGGCGAGGCCGTGCCC
GACGACCTGTACATCAAGGGCAGCGGCAACACCGCCGTGATCCAGAGCAGCGCCTTCTTCCCCACCCCCAG
CGGCAGCATCGTGACCAGCGAGAGCCAGCTGTTCAACAAGCCCTACTGGCTGCAGAGGGCCCAGGGCCACA
ACAACGGCATCTGCTGGGGCAACCAGCTGTTCGTGACCGTGGTGGACACCACCAGGAGCACCAACATGACC
CTGTGCACCGAGGTGACCAAGGAGGGCACCTACAAGAACGACAACTTCAAGGAGTACGTGAGGCACGTGGA
GGAGTACGACCTGCAGTTCGTGTTCCAGCTGTGCAAGATCACCCTGACCGCCGAGATCATGACCTACATCC
ACACCATGGACAGCAACATCCTGGAGGACTGGCAGTTCGGCCTGACCCCCCCCCCCAGCGCCAGCCTGCAG
GACACCTACAGGTTCGTGACCAGCCAGGCCATCACCTGCCAGAAGACCGCCCCCCCCAAGGAGAAGGAGGA
CCCCCTGAACAAGTACACCTTCTGGGAGGTGAACCTGAAGGAGAAGTTCAGCGCCGACCTGGACCAGTTCC
CCCTGGGCAGGAAGTTCCTGCTGCAGAGCGGCCTGAAGGCCAAGCCCAGGCTGAAGAGGAGCGCCCCCACC
ACCAGGGCCCCCAGCACCAAGAGGAAGAAGGTGAAGAAGTGA Sequence 12 (SEQ ID NO: 12):
ATGAGCGTGTGGAGGCCCAGCGAGGCCACCGTGTACCTGCCCCCCGTGCCCGTGAGCAAGGTGGTGAGCAC
CGACGAGTACGTGAGCAGGACCAGCATCTACTACTACGCCGGCAGCAGCAGGCTGCTGGCCGTGGGCAACC
CCTACTTCAGCATCAAGAGCCCCAACAACAACAAGAAGGTGCTGGTGCCCAAGGTGAGCGGCCTGCAGTAC
AGGGTGTTCAGGGTGAGGCTGCCCGACCCCAACAAGTTCGGCTTCCCCGACACCAGCTTCTACAACCCCGA
CACCCAGAGGCTGGTGTGGGCCTGCGTGGGCCTGGAGATCGGCAGGGGCCAGCCCCTGGGCGTGGGCGTGA
GCGGCCACCCCTACCTGAACAAGTTCGACGACACCGAGACCAGCAACAGGTACCCCGCCCAGCCCGGCAGC
GACAACAGGGAGTGCCTGAGCATGGACTACAAGCAGACCCAGCTGTGCCTGATCGGCTGCAAGCCCCCCAC
CGGCGAGCACTGGGGCAAGGGCGTGGCCTGCAACAACAACGCCGCCGCCACCGACTGCCCCCCCCTGGAGC
TGTTCAACAGCATCATCGAGGACGGCGACATGGTGGACACCGGCTTCGGCTGCATGGACTTCGGCACCCTG
CAGGCCAACAAGAGCGACGTGCCCATCGACATCTGCAACAGCACCTGCAAGTACCCCGACTACCTGAAGAT
GGCCAGCGAGCCCTACGGCGACAGCCTGTTCTTCTTCCTGAGGAGGGAGCAGATGTTCGTGAGGCACTTCT
TCAACAGGGCCGGCAAGCTGGGCGAGGCCGTGCCCGACGACCTGTACATCAAGGGCAGCGGCAACACCGCC
GTGATCCAGAGCAGCGCCTTCTTCCCCACCCCCAGCGGCAGCATCGTGACCAGCGAGAGCCAGCTGTTCAA
CAAGCCCTACTGGCTGCAGAGGGCCCAGGGCCACAACAACGGCATCTGCTGGGGCAACCAGCTGTTCGTGA
CCGTGGTGGACACCACCAGGAGCACCAACATGACCCTGTGCACCGAGGTGACCAAGGAGGGCACCTACAAG
AACGACAACTTCAAGGAGTACGTGAGGCACGTGGAGGAGTACGACCTGCAGTTCGTGTTCCAGCTGTGCAA
GATCACCCTGACCGCCGAGATCATGACCTACATCCACACCATGGACAGCAACATCCTGGAGGACTGGCAGT
TCGGCCTGACCCCCCCCCCCAGCGCCAGCCTGCAGGACACCTACAGGTTCGTGACCAGCCAGGCCATCACC
TGCCAGAAGACCGCCCCCCCCAAGGAGAAGGAGGACCCCCTGAACAAGTACACCTTCTGGGAGGTGAACCT
GAAGGAGAAGTTCAGCGCCGACCTGGACCAGTTCCCCCTGGGCAGGAAGTTCCTGCTGCAGAGCGGCCTGA
AGGCCAAGCCCAGGCTGAAGAGGAGCGCCCCCACCACCAGGGCCCCCAGCACCAAGAGGAAGAAGGTGAAG
AAGTGA Sequence 13 (SEQ ID NO: 13):
ATGCCCGTGCCCGTGAGCAAGGTGGTGAGCACCGACGAGTACGTGAGCAGGACCAGCATCTACTACTACGC
CGGCAGCAGCAGGCTGCTGGCCGTGGGCAACCCCTACTTCAGCATCAAGAGCCCCAACAACAACAAGAAGG
TGCTGGTGCCCAAGGTGAGCGGCCTGCAGTACAGGGTGTTCAGGGTGAGGCTGCCCGACCCCAACAAGTTC
GGCTTCCCCGACACCAGCTTCTACAACCCCGACACCCAGAGGCTGGTGTGGGCCTGCGTGGGCCTGGAGAT
CGGCAGGGGCCAGCCCCTGGGCGTGGGCGTGAGCGGCCACCCCTACCTGAACAAGTTCGACGACACCGAGA
CCAGCAACAGGTACCCCGCCCAGCCCGGCAGCGACAACAGGGAGTGCCTGAGCATGGACTACAAGCAGACC
CAGCTGTGCCTGATCGGCTGCAAGCCCCCCACCGGCGAGCACTGGGGCAAGGGCGTGGCCTGCAACAACAA
CGCCGCCGCCACCGACTGCCCCCCCCTGGAGCTGTTCAACAGCATCATCGAGGACGGCGACATGGTGGACA
CCGGCTTCGGCTGCATGGACTTCGGCACCCTGCAGGCCAACAAGAGCGACGTGCCCATCGACATCTGCAAC
AGCACCTGCAAGTACCCCGACTACCTGAAGATGGCCAGCGAGCCCTACGGCGACAGCCTGTTCTTCTTCCT
GAGGAGGGAGCAGATGTTCGTGAGGCACTTCTTCAACAGGGCCGGCAAGCTGGGCGAGGCCGTGCCCGACG
ACCTGTACATCAAGGGCAGCGGCAACACCGCCGTGATCCAGAGCAGCGCCTTCTTCCCCACCCCCAGCGGC
AGCATCGTGACCAGCGAGAGCCAGCTGTTCAACAAGCCCTACTGGCTGCAGAGGGCCCAGGGCCACAACAA
CGGCATCTGCTGGGGCAACCAGCTGTTCGTGACCGTGGTGGACACCACCAGGAGCACCAACATGACCCTGT
GCACCGAGGTGACCAAGGAGGGCACCTACAAGAACGACAACTTCAAGGAGTACGTGAGGCACGTGGAGGAG
TACGACCTGCAGTTCGTGTTCCAGCTGTGCAAGATCACCCTGACCGCCGAGATCATGACCTACATCCACAC TABLE 1 -continued Depiction of sequences SEQ ID NO:depiction CATGGACAGCAACATCCTGGAGGACTGGCAGTTCGGCCTGACCCCCCCCCCAGCGCCAGCCTGCAGGACA
CCTACAGGTTCGTGACCAGCCAGGCCATCACCTGCCAGAAGACCGCCCCCCCCAAGGAGAAGGAGGACCCC
CTGAACAAGTACACCTTCTGGGAGGTGAACCTGAAGGAGAAGTTCAGCGCCGACCTGGACCAGTTCCCCCT
GGGCAGGAAGTTCCTGCTGCAGAGCGGCCTGAAGGCCAAGCCCAGGCTGAAGAGGAGCGCCCCCACCACCA
GGGCCCCCAGCACCAAGAGGAAGAAGGTGAAGAAGTAA Sequence 14 (SEQ ID NO: 14):
ATGTACTACGCCGGCAGCAGCAGGCTGCTGGCCGTGGGCAACCCCTACTTCAGCATCAAGAGCCCCAACAA
CAACAAGAAGGTGCTGGTGCCCAAGGTGAGCGGCCTGCAGTACAGGGTGTTCAGGGTGAGGCTGCCCGACC
CCAACAAGTTCGGCTTCCCCGACACCAGCTTCTACAACCCCGACACCCAGAGGCTGGTGTGGGCCTGCGTG
GGCCTGGAGATCGGCAGGGGCCAGCCCCTGGGCGTGGGCGTGAGCGGCCACCCCTACCTGAACAAGTTCGA
CGACACCGAGACCAGCAACAGGTACCCCGCCCAGCCCGGCAGCGACAACAGGGAGTGCCTGAGCATGGACT
ACAAGCAGACCCAGCTGTGCCTGATCGGCTGCAAGCCCCCCACCGGCGAGCACTGGGGCAAGGGCGTGGCC
TGCAACAACAACGCCGCCGCCACCGACTGCCCCCCCCTGGAGCTGTTCAACAGCATCATCGAGGACGGCGA
CATGGTGGACACCGGCTTCGGCTGCATGGACTTCGGCACCCTGCAGGCCAACAAGAGCGACGTGCCCATCG
ACATCTGCAACAGCACCTGCAAGTACCCCGACTACCTGAAGATGGCCAGCGAGCCCTACGGCGACAGCCTG
TTCTTCTTCCTGAGGAGGGAGCAGATGTTCGTGAGGCACTTCTTCAACAGGGCCGGCAAGCTGGGCGAGGC
CGTGCCCGACGACCTGTACATCAAGGGCAGCGGCAACACCGCCGTGATCCAGAGCAGCGCCTTCTTCCCCA
CCCCCAGCGGCAGCATCGTGACCAGCGAGAGCCAGCTGTTCAACAAGCCCTACTGGCTGCAGAGGGCCCAG
GGCCACAACAACGGCATCTGCTGGGGCAACCAGCTGTTCGTGACCGTGGTGGACACCACCAGGAGCACCAA
CATGACCCTGTGCACCGAGGTGACCAAGGAGGGCACCTACAAGAACGACAACTTCAAGGAGTACGTGAGGC
ACGTGGAGGAGTACGACCTGCAGTTCGTGTTCCAGCTGTGCAAGATCACCCTGACCGCCGAGATCATGACC
TACATCCACACCATGGACAGCAACATCCTGGAGGACTGGCAGTTCGGCCTGACCCCCCCCCCAGCGCCAG
CCTGCAGGACACCTACAGGTTCGTGACCAGCCAGGCCATCACCTGCCAGAAGACCGCCCCCCCCAAGGAGA
AGGAGGACCCCCTGAACAAGTACACCTTCTGGGAGGTGAACCTGAAGGAGAAGTTCAGCGCCGACCTGGAC
CAGTTCCCCCTGGGCAGGAAGTTCCTGCTGCAGAGCGGCCTGAAGGCCAAGCCCAGGCTGAAGAGGAGCGC
CCCCACCACCAGGGCCCCCAGCACCAAGAGGAAGAAGGTGAAGAAGTGA Sequence 15 (SEQ ID NO: 15):
ATGGTGGGCAACCCCTACTTCAGCATCAAGAGCCCCAACAACAACAAGAAGGTGCTGGTGCCCAAGGTGAG
CGGCCTGCAGTACAGGGTGTTCAGGGTGAGGCTGCCCGACCCCAACAAGTTCGGCTTCCCCGACACCAGCT
TCTACAACCCCGACACCCAGAGGCTGGTGTGGGCCTGCGTGGGCCTGGAGATCGGCAGGGGCCAGCCCCTG
GGCGTGGGCGTGAGCGGCCACCCCTACCTGAACAAGTTCGACGACACCGAGACCAGCAACAGGTACCCCGC
CCAGCCCGGCAGCGACAACAGGGAGTGCCTGAGCATGGACTACAAGCAGACCCAGCTGTGCCTGATCGGCT
GCAAGCCCCCCACCGGCGAGCACTGGGGCAAGGGCGTGGCCTGCAACAACAACGCCGCCGCCACCGACTGC
CCCCCCCTGGAGCTGTTCAACAGCATCATCGAGGACGGCGACATGGTGGACACCGGCTTCGGCTGCATGGA
CTTCGGCACCCTGCAGGCCAACAAGAGCGACGTGCCCATCGACATCTGCAACAGCACCTGCAAGTACCCCG
ACTACCTGAAGATGGCCAGCGAGCCCTACGGCGACAGCCTGTTCTTCTTCCTGAGGAGGGAGCAGATGTTC
GTGAGGCACTTCTTCAACAGGGCCGGCAAGCTGGGCGAGGCCGTGCCCGACGACCTGTACATCAAGGGCAG
CGGCAACACCGCCGTGATCCAGAGCAGCGCCTTCTTCCCCACCCCCAGCGGCAGCATCGTGACCAGCGAGA
GCCAGCTGTTCAACAAGCCCTACTGGCTGCAGAGGGCCCAGGGCCACAACAACGGCATCTGCTGGGGCAAC
CAGCTGTTCGTGACCGTGGTGGACACCACCAGGAGCACCAACATGACCCTGTGCACCGAGGTGACCAAGGA
GGGCACCTACAAGAACGACAACTTCAAGGAGTACGTGAGGCACGTGGAGGAGTACGACCTGCAGTTCGTGT
TCCAGCTGTGCAAGATCACCCTGACCGCCGAGATCATGACCTACATCCACACCATGGACAGCAACATCCTG
GAGGACTGGCAGTTCGGCCTGACCCCCCCCCCAGCGCCAGCCTGCAGGACACCTACAGGTTCGTGACCAG
CCAGGCCATCACCTGCCAGAAGACCGCCCCCCCCAAGGAGAAGGAGGACCCCCTGAACAAGTACACCTTCT
GGGAGGTGAACCTGAAGGAGAAGTTCAGCGCCGACCTGGACCAGTTCCCCCTGGGCAGGAAGTTCCTGCTG
CAGAGCGGCCTGAAGGCCAAGCCCAGGCTGAAGAGGAGCGCCCCCACCACCAGGGCCCCCAGCACCAAGAG
GAAGAAGGTGAAGAAGTGA Sequence 16 (SEQ ID NO: 16):
CATATgAccgTgTAccTgccc Sequence 17 (SEQ ID NO: 17):
gTCgACTTACTTCTTCACCTTCTTCC

SPECIFIC MODES FOR CARRYING OUT THE INVENTION

The present invention is further illustrated in detail by reference to the examples as follows. It is understood by those skilled in the art that the examples are used only for the purpose of illustrating the present invention, rather than limiting the protection scope of the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3$^{rd}$ Edition, John Wiley & Sons, Inc., 1995, or in accordance with the product instructions. The reagents and instruments used in the present invention without marking out their manufacturers are all conventional products commercially available from markets. Those skilled in the art understand that the examples are used for illustrating the present invention, but not intended to limit the protection scope of the present invention.

Example 1: Expression of the Truncated HPV58 L1 Proteins with a Sequence as Set Forth in SEQ ID NO:1

Preparation of Full-Length HPV58 L1 Gene as a Template
The full-length HPV58 L1 gene as a template was synthesized by Shanghai Boya Bio Co. The synthesized gene fragment has a full length of 1575 bp, and its sequence is as set forth in SEQ ID NO:8. On the basis of the synthetic full-length HPV58 L1 gene fragment, the polynucleotides encoding the truncated HPV58 L1 proteins according to the invention were prepared.

Construction of Non-Fusion Expression Vectors for Expressing the Truncated HPV58 L1 Proteins The full-length HPV58 L1 gene as synthesized in the previous step was used as the template for the PCR reaction. The forward primer was 58N35F: 5'-cATATg Acc gTg TAc cTg ccc-3' (SEQ ID NO: 16), at the 5' terminal of which the restriction endonuclease NdeI site CAT ATG was introduced, wherein ATG was the initiation codon in *E. coli* system. The reverse primer was 58CR: 5'-gTCgAC TTA CTT CTT CAC CTT CTT CC-3' (SEQ ID NO: 17), at the 5' terminal of which the restriction endonuclease SalI site was introduced. The PCR reaction was performed in a PCR thermocycler (Biometra T3) under the following conditions:

| | | |
|---|---|---|
| 94° C. | denaturation for 10 min | 1 cycle |
| 94° C. | denaturation for 50 sec | 15 cycles |
| 56° C. | annealing for 50 sec | |
| 72° C. | elongation for 1.5 min | |
| 72° C. | elongation for 10 min | 1 cycle |

The DNA fragments, about 1.5 kb in length, were obtained after amplification. The PCR products were linked into the commercially available pMD 18-T vector (Takara Biosciences), and were then transformed into *E. coli* DH5α. Positive bacterial colonies were screened, and plasmids were extracted. After digestion with NdeI/SalI, it was identified that positive clones, designated as pMD 18-T-HPV58N35C-L1, were obtained, wherein the truncated HPV58 L1 gene was inserted.

The nucleotide sequence of the fragment of interest, which was inserted into the plasmid pMD 18-T-HPV58N35C-L1, was determined as SEQ ID NO:9 by Shanghai Boya Bio Co. using M13 (+)/(−) primers, and the amino acid sequence encoded thereby was set forth in SEQ ID NO:1. The sequence corresponded to a HPV58 L1 protein having 35 amino acids truncated at its N-terminal and no amino acid truncated at its C-terminal, designated as HPV58N35C-L1.

The HPV58N35C-L1 gene fragment was obtained by NdeI/SalI digestion of the plasmid pMD 18-T-HPV58N35C-L1. The fragment was linked to the non-fusion expression vector pT0-T7 (Luo wenxin et al. Chinese Journal of Biotechnology, 2000, 16: 53-57) digested with NdeI/SalI, and was then transformed into *E. coli* ER2566. Positive bacterial colonies were screened, and plasmids were extracted. After digestion with NdeI/SalI, it was identified that positive clones, designated as pT0-T7-HPV58N35C-L1, were obtained, wherein the fragment of interest was inserted.

1 μl of the plasmid pT0-T7-HPV58N35C-L1 (0.15 mg/ml) was taken to transform 40 μL competent *E. coli* ER2566 (purchased from New England Biolabs) prepared by Calcium chloride method, and then the bacteria were plated on solid LB medium (the components of the LB medium: 10 g/L peptone, 5 g/L yeast powder, and 10 g/L NaCl, the same as below) containing kanamycin (at a final concentration of 25 mg/ml, the same as below). Plates were statically incubated at 37° C. for about 10-12 h until single colonies could be observed clearly. Single colonies from the plates were transferred to a tube containing 4 ml liquid LB media containing kanamycin. Cultures were incubated in a shaking incubator at 220 rpm for 10 h at 37° C., and then 1 ml bacterial solution was taken and stored at −70° C.

Expression of HPV58N35C-L1 Protein on Large Scale

The *E. coli* solution carrying the recombinant plasmid pTO-T7-HPV58N35C-L1 at −70° C. as prepared in the previous step was seeded in 50 mL LB liquid medium containing kanamycin and incubated at 200 rpm and 37° C. for about 8 h. Then, the cultures were transferred to ten flasks (5 ml cultures per flask), each of which contained 500 mL LB medium containing kanamycin, and then were incubated in a shaking incubator overnight at 200 rpm and 37° C., as a starter culture.

A 50 L fermenter made by Shanghai Baoxing Biological Ltd was used in large-scale culture. PH electrode of the fermenter was calibrated. 30 L LB medium was loaded into the fermenter, in situ sterilized at 121° C. for 30 minutes. Oxygen-dissolved electrode was calibrated, wherein the value was determined as 0 prior to introduction of air after sterilization and as 100% prior to vaccination after introduction of air while stirring at an initial rate of 100 rpm.

Preparation of the feed: The mixture of peptone and yeast extract at a concentration of 30% is prepared (20 g peptone and 10 g yeast extract were dissolved in 100 mL); a glucose solution of 50% is prepared (50 g glucose was dissolved in 100 ml). The two solutions were sterilized at 121° C. for 20 min.

On the next day, the starter cultures in the ten flasks (for a total of 5 L) were transferred to the fermenter. A temperature of 37° C. and a pH value of 7.0 were set, the dissolved $O_2$ was maintained at >40% by regulating agitation rate and air supply manually.

Flow Feed: the glucose solution (50%) and the mixture of peptone and yeast extract (30%) were mixed at a solute mass ratio of 2:1.

Flow rates were as followed (25 ml/min was defined as 100%):

$1^{st}$ h: 5%
$2^{nd}$ h: 10%
$3^{rd}$ h: 20%
$4^{th}$ h: 40%
$5^{th}$ h to the end: 60%

When the bacterial concentration reached an $OD_{600}$ of about 10.0, the culturing temperature was lowered to 25° C. and 4 g IPTG was added to initiate an induction culture of 4 h. Fermentation was halted when the final concentration reached an $OD_{600}$ of about 60. The bacteria were collected by centrifugation. The bacteria expressing HPV58N35C-L1 protein were obtained, weighted about 2.5 kg.

Example 2: Preparation of HPV58N35C-L1 Protein with a Purity of about 70%

Bacteria were re-suspended at a proportion of 1 g bacteria corresponding to 10 ml lysis buffer (20 mM Tris buffer pH 7.2, 300 mM NaCl). Bacteria were disrupted by an APV homogenizer (Invensys Group) for five times at a pressure of 600 bar. The homogenate was centrifuged at 13,500 rpm (30,000 g) using JA-14 rotor for 15 min, and the supernatant (i.e. the supernatant of disrupted bacteria) was obtained. The supernatant was subjected to 10% SDS-PAGE. At this stage, the HPV58N35C-L1 protein in the supernatant had a purity of about 10% (see FIG. 1, Lane 1).

The supernatant was dialyzed by a CENTRASETTE 5 Tangential Flow Filter (Pall Co.) running at a pressure of 0.5 psi, a flow rate of 500 ml/min, and a tangential flow rate of 200 mL/min, wherein the membrane retention molecular weight was 30 kDa, the dialysis solution was 10 mM phosphate buffer pH 6.0, and the dialysis volume was three times of the volume of the supernatant.

After thorough dialysis, the mixture was centrifuged at 9500 rpm (12,000 g) using JA-10 rotor (Beckman J25 high speed centrifuge)) for 20 min, and the precipitate (i.e. the precipitate product free of salts) was collected. The precipitate was re-suspended in 20 mM phosphate buffer (pH 8.0) containing 20 mM DTT and 600 mM NaCl, wherein the volume of the buffer was 1/10 of the volume of the supernatant. The mixture was stirred for 30 min and centrifuged at 13,500 rpm (30,000 g) using JA-14 rotor (Beckman J25 high speed centrifuge) for 20 min. The supernatant and precipitate (i.e. the precipitate obtained after re-dissolution) were collected. The supernatant was diluted with 20 mM phosphate buffer (pH 8.0) containing 20 mM DTT of an equal volume, resulting in the final NaCl concentration of 0.3 M. Then, the diluted supernatant was filtered using a filter membrane with an aperture of 0.22 μm. The sample obtained (i.e. re-dissolved supernatant) was purified by cation exchange chromatography (as described in Example 3). 30 μL of 6× loading buffer (12% (w/v) SDS, 0.6% (w/v) bromophenol blue, 0.3M Tris-HCl pH 6.8, 60% (v/v) glycerin, 5% (v/v) β-mercaptoethanol) was added to 150 μL filtered supernatant, and the result solution was mixed homogeneously and was placed in a water bath at 80° C. for 10 min. Then, 10 μl sample was subjected to 10% SDS-PAGE at 120V for 120 min. The electrophoretic bands were stained by Coomassie brilliant blue. The electrophoretic result was shown in FIG. 1. The result showed that HPV58N35C-L1 protein was purified and enriched after the steps of precipitation and re-dissolution, with its purity increased from about 10% to about 70% (see FIG. 1, Lane 1 and Lane 3).

Example 3: Chromatographic Purification of HPV58N35C-L1 Protein

1) Purification of HPV58N35C-L1 Protein by Cation Exchange Chromatography

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.)

Column Volume: 5.5 cm×20 cm

Buffer: 20 mM phosphate buffer pH 8.0, 20 mM DTT
20 mM phosphate buffer pH 8.0, 20 mM DTT, 2M NaCl Flow Rate: 25 mL/min Detector Wavelength: 280 nm Sample: about 70% pure HPV58N35C-L1 protein solution, as filtered through a filter membrane with an aperture of 0.22 μm in Example 2.

Elution protocol: eluting undesired proteins with 500 mM NaCl, eluting the protein of interest with 1000 mM NaCl, collecting eluate eluted with 1000 mM NaCl, and finally getting about 900 mL purified HPV58N35C-L1 sample.

2) Purification of HPV58N35C-L1 by CHT-II Chromatography (Hydroxyapatite Chromatography)

Equipment: AKTA Explorer 100 preparative liquid chromatography system produced by GE Healthcare (i.e. the original Amershan Pharmacia Co.)

Chromatographic media: CHT-II (purchased from Bio-Rad)

Column Volume: 5.5 cm×20 cm

Buffer: 20 mM phosphate buffer pH8.0, 20 mM DTT,
20 mM phosphate buffer pH 8.0, 20 mM DTT, 2M NaCl Flow Rate: 20 mL/min Detector Wavelength: 280 nm Sample: 1000 mM NaCl elution product obtained in the previous step, diluted to a NaCl concentration of 0.3M with 20 mM phosphate buffer pH 8.0, 20 mM DTT.

Elution protocol: eluting undesired proteins with 500 mM NaCl, eluting the protein of interest with 1000 mM NaCl, collecting eluate eluted with 1000 mM NaCl, and finally getting 800 mL purified HPV58N35C-L1 sample.

Figure 2:
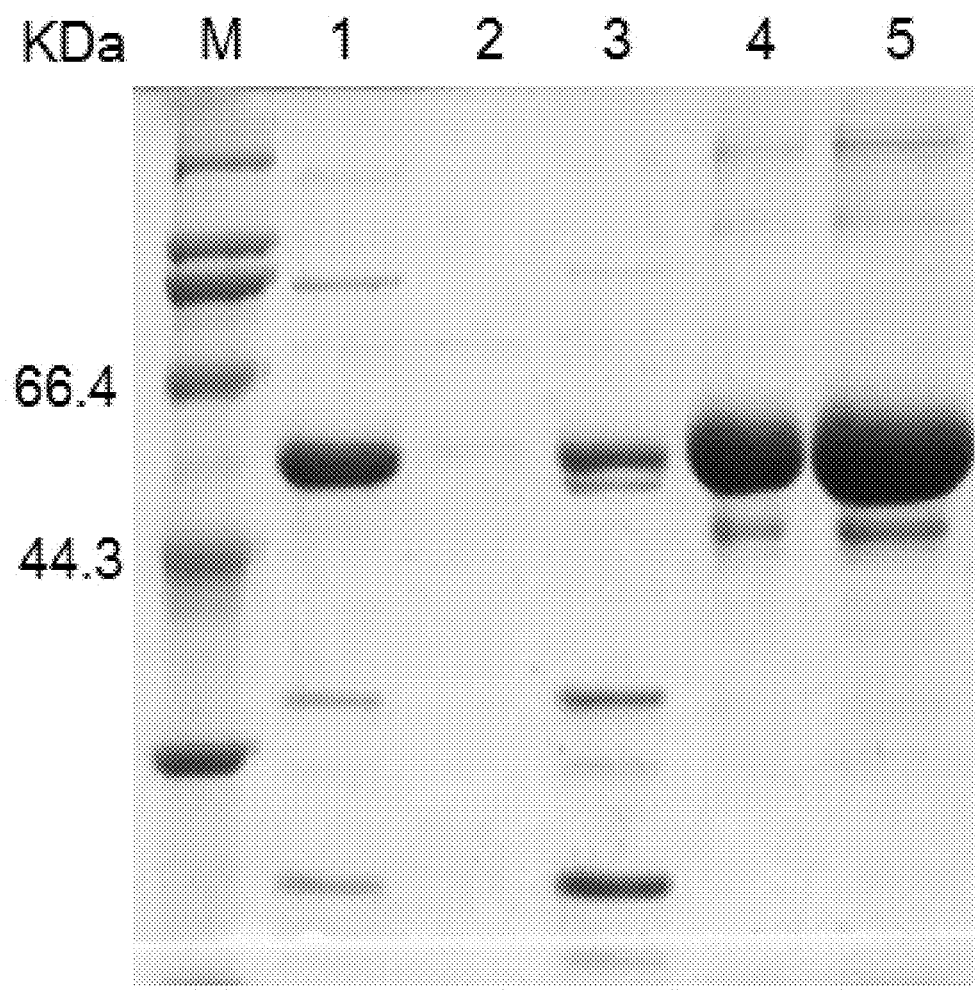
FIG. 2 shows the SDS-PAGE result of HPV58N35C-L1 purified by cation exchange chromatography and CHT-II (hydroxyapatite chromatography) in Example 3. Lane M: protein molecular weight marker; Lane 1: sample before purification with CHT-II column; Lane 2: flow-through fraction during purification with CHT-II column; Lane 3: elution fraction eluted with 500 mmol/L NaCl; Lane 4: elution fraction eluted with 1000 mmol/L NaCl (the loading volume was 10 μL); Lane 5: elution fraction eluted with 1000 mmol/L NaCl (the loading volume was 20 μL). The result showed that after purification with CHT-II, HPV58N35C-L1 protein eluted with 1000 mmol/L NaCl reached a purity of about 98%.

30 μL 6× loading buffer was added to 150 μL HPV58N35C-L1 sample as purified by the method in the present Example, and then the result solution was mixed homogeneously. After incubating the solution in a water bath at 80° C. for 10 min, a 10 μL sample was subjected to 10% SDS-PAGE at 120V for 120 min. The electrophoretic bands were stained by Coomassie brilliant blue. The electrophoretic result was shown in FIG. 2. The result showed that after said purification step, the concentration of HPV58N35C-L1 protein was about 1.0 mg/ml, with a purity of greater than 98%.

Example 4: Assembly of HPV58N35C-L1 VLPs

Equipment: CENTRASETTE 5 Tangential Flow Filter (Pall Co.), wherein the membrane retention molecular weight was 30 kDa. Sample: HPV58N35C-L1 with a purity of greater than 98% as obtained in Example 3.

Sample Renaturation: Sample buffer was exchanged with 10 L renaturation buffer (50 mM PB (sodium phosphate buffer) pH 6.0, 2 mM $CaCl_2$, 2 mM $MgCl_2$, 0.5M NaCl, 0.003% Tween-80) thoroughly. The Tangential Flow Filter was run at a pressure of 0.5 psi and a tangential flow rate of 10 mL/min. When the exchange with renaturation buffer was finished, the renaturation buffer was exchanged with storage buffer (20 L PBS: 20 mM PB pH 6.5, 0.5M NaCl) with an exchange volume of 20 L. The Tangential Flow Filter was run at a pressure of 0.5 psi and a tangential flow rate of 25 mL/min. When the exchange was finished, the sample was aseptically filtrated with a Pall filter (0.20 μm), and thereby obtaining HPV58N35C-L1 VLPs. The HPV58N35C-L1 VLPs were stored at 4° C. for further use.

Figure 3:
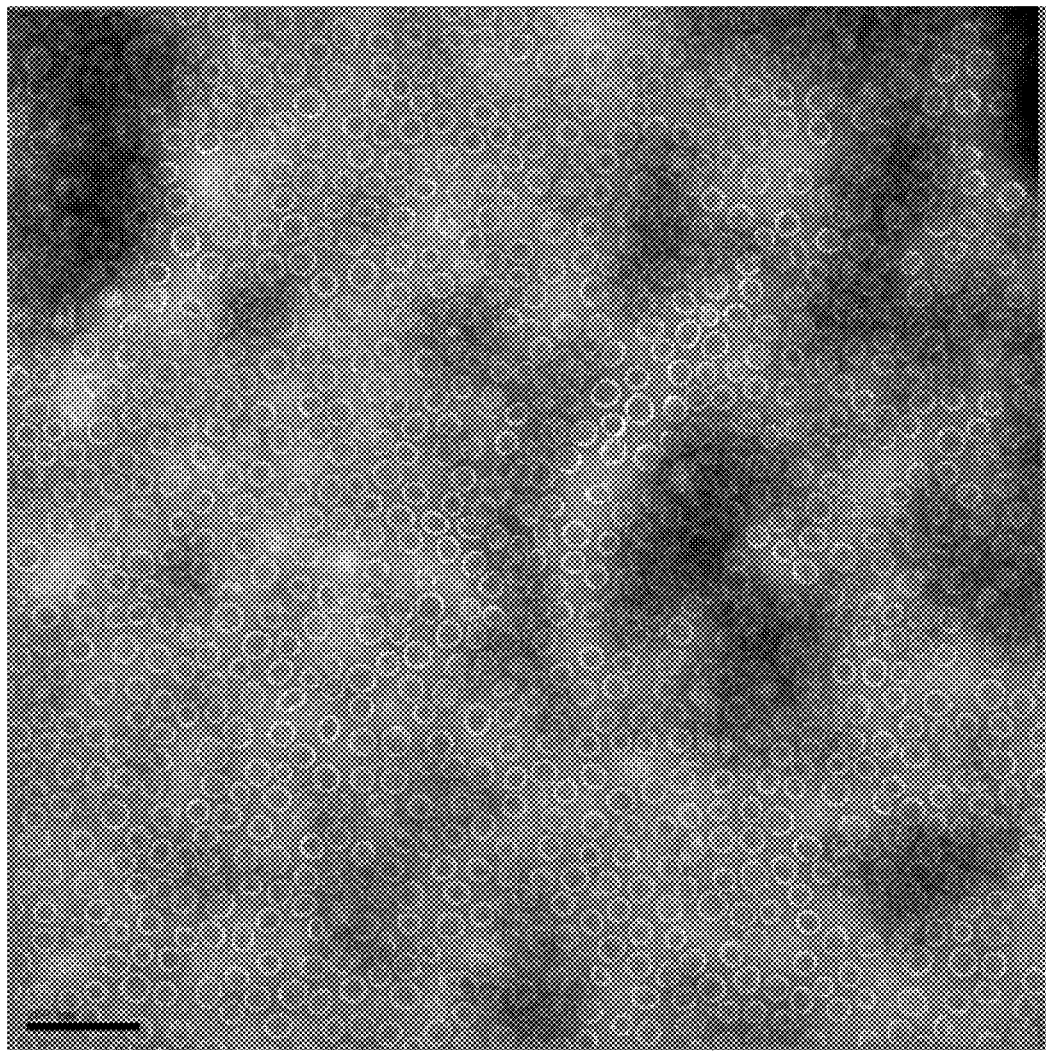
FIG. 3 shows the transmission electron microscopy (TEM) photograph of HPV58N35C-L1 VLPs obtained in Example 4 (taken at 50,000× magnification, Bar=0.2 μm). A large number of VLPs with a radius of about 25 nm were observed in visual field, wherein the particle size was consistent with the theoretic size and the particles were homogenous.

Example 5: Determination of the Morphology of HPV58N35C-L1 VLPs and Determination of Immunogenicity Thereof Transmission Electron Microscopy (TEM) of HPV58N35C-L1 VLPs The equipment was a JEOL 100 kV Transmission Electron Microscope (100,000× magnification). HPV58N35C-L1 VLPs obtained in Example 4 were negatively stained with 2% phosphotungstic acid at pH 7.0, and fixed on a copper grid for observation. Results were shown in FIG. 3. A large number of VLPs with a radius of approximately 25 nm, which were homogenous and in a hollow form, were observed.

Dynamic Light-Scattering Measurement of HPV58N35C-L1 VLPs

Figure 4:
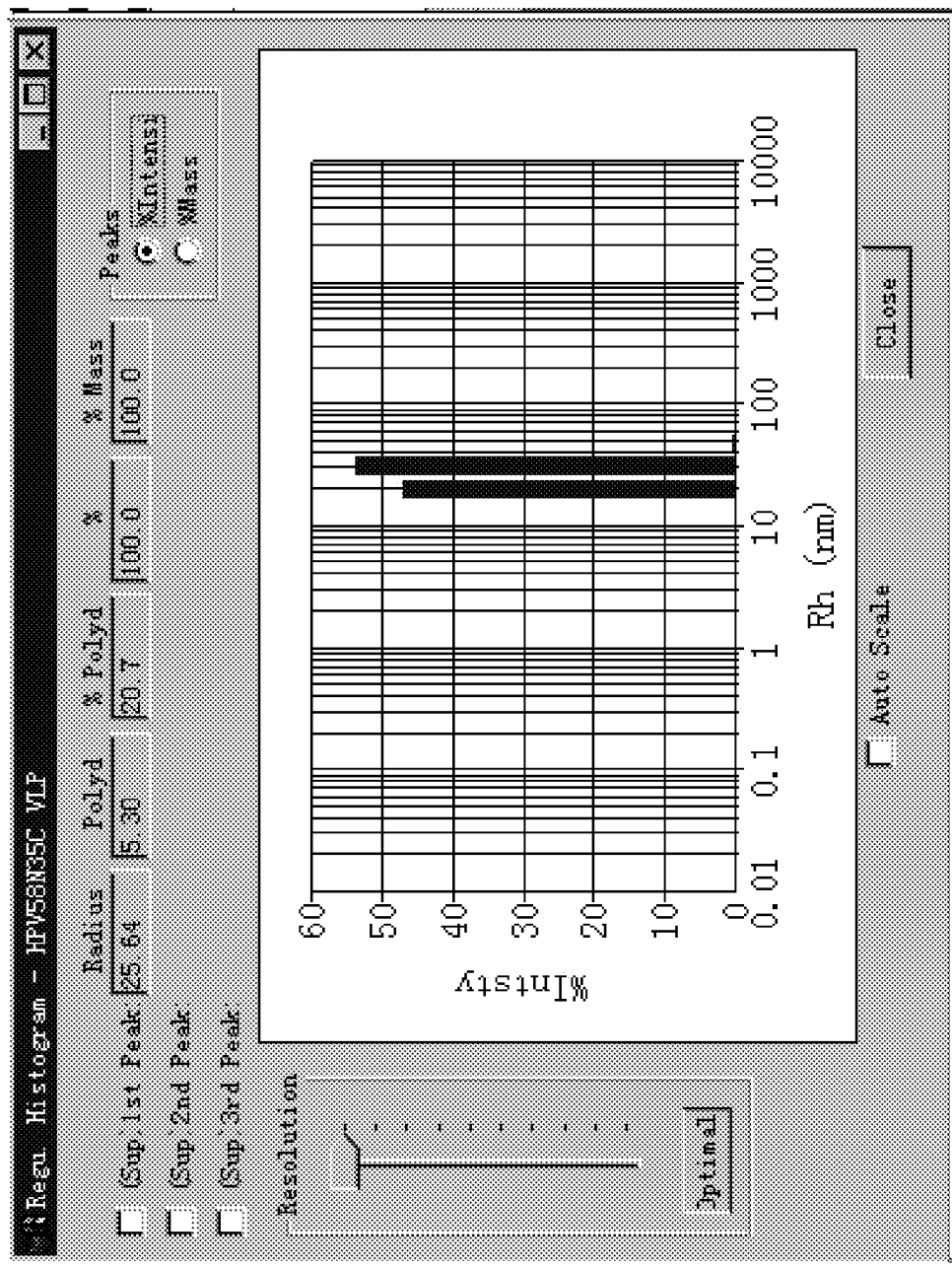
FIG. 4 shows the dynamic light-scattering measurement result of HPV58N35C-L1 VLPs obtained in Example 4. The result showed that HPV58N35C-L1 VLPs had a hydrodynamic radius of 25.64 nm and a particle assembly rate of 100%.

DynaPro MS/X dynamic light-scattering instrument (including a temperature controller) (US Protein Solutions Co.) was used for light-scattering measurements. The regulation algorithm was used in the measurements. The sample was the HPV58N35C-L1 VLPs obtained in Example 4. The sample was passed through a 0.22 μm filter membrane prior to the measurement. The result was shown in FIG. 4. The result showed that HPV58N35C-L1 VLPs had a Hydrodynamic radius of 25.64 nm.

Establishment of a Cellular Model for HPV58 Pseudovirion Neutralization

HPV can hardly be cultured in vitro, and the HPV host is strongly specific. Thus, HPV can hardly be propagated in hosts other than human. That is, there was not an appropriate animal model for HPV. Therefore, in order to evaluate the immune protection of HPV vaccines quickly, it is urgent to establish an effective model for in vitro neutralization assays.

In Vitro Model of Pseudovirion Infection: by means of the characteristic that HPV VLP can package nucleic acids non-specifically, HPV pseudovirion was formed by expressing HPV L1 and L2 protein in cells, and by packaging episomal viral DNA or reporter plasmids introduced heterologously (Yeager, M. D, Aste-Amezaga, M. et al (2000) Virology (278) 570-7). The concrete methods include methods of recombinant viral expression systems and methods of co-transfection of multi-plasmids. Methods of co-transfection of multi-plasmids were used in the Example exemplarily.

In addition, some improvement directed to HPV systems were made by conventional methods as followed. The calcium phosphate transfection method for 293FT cell line was optimized to obtain a transfection efficiency of up to more than 90%, thereby facilitating large-scale production. The expression plasmid for expressing HPV structural proteins was codon-optimized to express HPV L1 and L2 gene efficiently in mammalian cells, thereby facilitating high efficient assembly of pseudovirion.

Construction of HPV Pseudovirion was as follows:

Plasmid p58L1h (the pAAV vector carrying the nucleotide sequence encoding HPV58 L1 protein (NCBI database, Accession Number: P26535.1)), plasmid p58L2h (the pAAV vector carrying the nucleotide sequence encoding HPV58 L2 protein (NCBI database, Accession Number: P26538.1)), and plasmid pN31-EGFP carrying green fluorescent protein gene, were purified by CsCl density gradient centrifugation, wherein said pN31-EGFP and said pAAV vectors were donated by Professor John T. Schiller of NIH. Methods for purifying plasmids using CsCl density gradient centrifugation were well known in the art (see The Molecular Cloning Experiment Guide, 3rd edition).

293FT cells (Invitrogen) cultured on a 10 cm cell culture plate were co-transfected with the purified p58L1h, p58L2h and pN31-EGFP (40 μg for each) by calcium phosphate transfection method. Calcium phosphate transfection method was well known in the art (see The Molecular Cloning Experiment Guide, 3rd edition). In brief, p58L1h, p58L2h and pN31-EGFP (40 μg for each) were added to the mixture of 1 mL HEPES solution (125 μL 1M HEPES pH7.3 per 50 mL deionized water, stored at 4° C.) and 1 mL 0.5M CaCl$_2$ solution. After mixing homogeneously, 2 mL 2× HeBS solution (0.28M NaCl (16.36 g), 0.05M HEPES (11.9 g), and 1.5 mM Na$_2$HPO$_4$ (0.213 g), dissolved in 1000 mL deionized water, pH 6.96, stored at −70° C.) was added dropwise. After standing at room temperature for 1 min, the mixture was added to the 10 cm cell culture plate where the 293FT cells were cultured. After culturing for 6 hr, the original culture medium was decanted and 10 ml fresh complete medium (Invitrogen Co.) was added. After transfection for 48 hours, the medium was decanted and the cells were washed twice with PBS. Then, the cells were collected and counted. Every $10^8$ cells were re-suspended in 1 mL lysis solution (0.25% Brij58, 9.5 mM MgCl$_2$). After lysing, cell lysate was centrifuged at 5,000 g for 10 min and the supernatant was collected. The Pseudovirion solution was obtained after adding 5M NaCl to a final concentration of 850 mM, and then was stored in small packages at −20° C.

Determination of the Neutralization Titers of Antibodies

293FT cells (Invitrogen) were plated on a 96-well cell culture plate ($1.5 \times 10^4$ cells/well). Neutralization assay was performed five hours later. Serum samples comprising antibodies to be tested were serially diluted with 10% DMEM half-by-half. The diluted samples (50 μL for each) were respectively mixed with 50 μL Pseudovirion solution diluted in 10% DMEM as prepared above (moi=0.1). After incubating at 4° C. for 1 h, the mixture was added to the 96-well cell culture plate with 293FT cells. The mixture was then incubated for 72 h at 37° C. Antibody titers of samples were estimated by observing fluorescence. Infection percentage of cells in each well was then checked by flow cytometry (EPICS XL, American Beckman Coulter Co.). The exact antibody titers of serums were calculated. Infection percentage was the percentage of cells in the positive region of the cell sample to be tested minus that in the positive region of the uninfected control cell sample.

Infection-inhibition percentage=(1−infection percentage of wells with serum/infection percentage of wells without serum)×100%

The positive region was defined as the cell region having a GFP signal determined by flow cytometry at least 10 times higher than the signal of the control cells.

Neutralization titer of antibodies was defined as the highest dilution fold under which the infection-inhibition percentage reached above 50%. Antibodies were considered as having neutralizing capacity if their infection-inhibition percentage was above 50% after 50 times dilutions.

Evaluation of Immune Protection of Vaccination of Animals with HPV58 VLPs

Rabbits were used to evaluate the immune protection of the HPV58 VLPs according to the invention. Animals for vaccination were 5 female rabbits (general grade), 6-8 weeks old, purchased from the Disease Prevention and Control Center of Guangxi province. HPV58N35C-L1 VLPs (at a concentration of 0.1 mg/ml) prepared in Example 4, were mixed with equal volume of complete Freund's Adjuvant for the first vaccination, or with equal volume of incomplete Freund's Adjuvant for the booster. The vaccination procedure was as followed: the first vaccination at Month 0, and the booster at Month 1, 2 and 3, respectively. Rabbits were vaccinated via muscle injection, with an amount of 200 μg HPV58N35C-L1 VLPs prepared in Example 4 per rabbit.

After the first vaccination, peripheral venous blood was collected every week, and serum was separated and stored for test. The neutralization titers of antibodies against HPV58 pseudovirion in the rabbit serum were determined by the method above.

Figure 5:
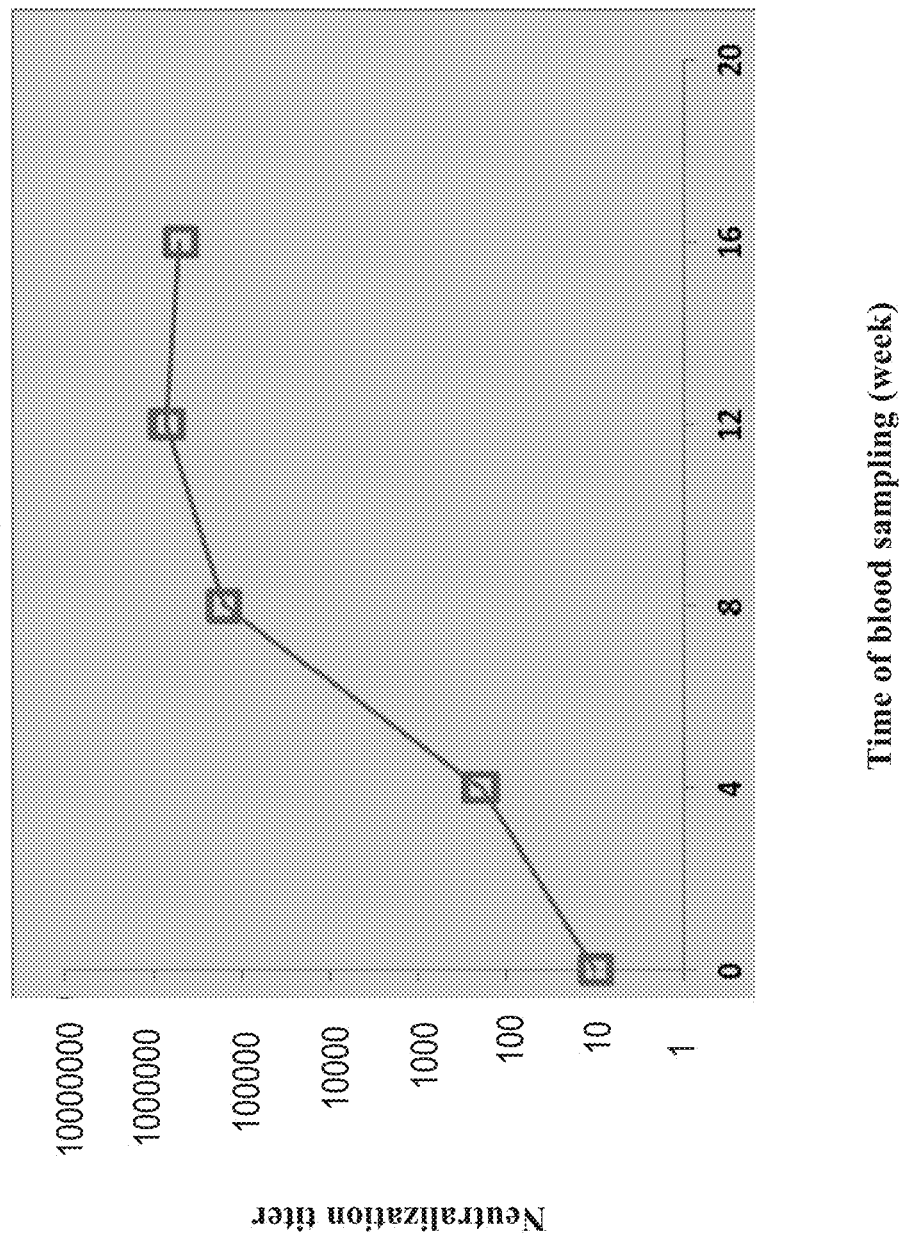
FIG. 5 shows neutralization titers of antibodies in serum at different stages after vaccination of rabbits with HPV58N35C-L1 VLPs as determined in Example 5. The neutralization titers of antibodies increased significantly 2 months after the first vaccination, and reached a peak level of $10^5$ after a booster. The longitudinal axis represents the neutralization titers of antibodies; the horizontal axis represents the time of blood sampling.

The result was shown in FIG. 5. FIG. 5 showed that neutralization titers of antibodies in serum at different stages after vaccination of rabbits with HPV58N35C-L1 VLPs prepared in Example 4. It could be seen that the neutralization titers of antibodies increased significantly 2 months after the first vaccination, and reached a peak level of $10^5$ after a booster. It suggested that HPV58N35C-L1 VLPs as prepared in Example 4 had good immunogenicity, could induce the generalization of neutralization antibodies against HPV58 with a high titer in animals, and could be used as an effective vaccine for the prevention of HPV58 infection. In addition to Freund's Adjuvant, other adjuvants well known in the art might also be used in the vaccines, for example, aluminum hydroxide or aluminum phosphate adjuvants.

Figure 6:
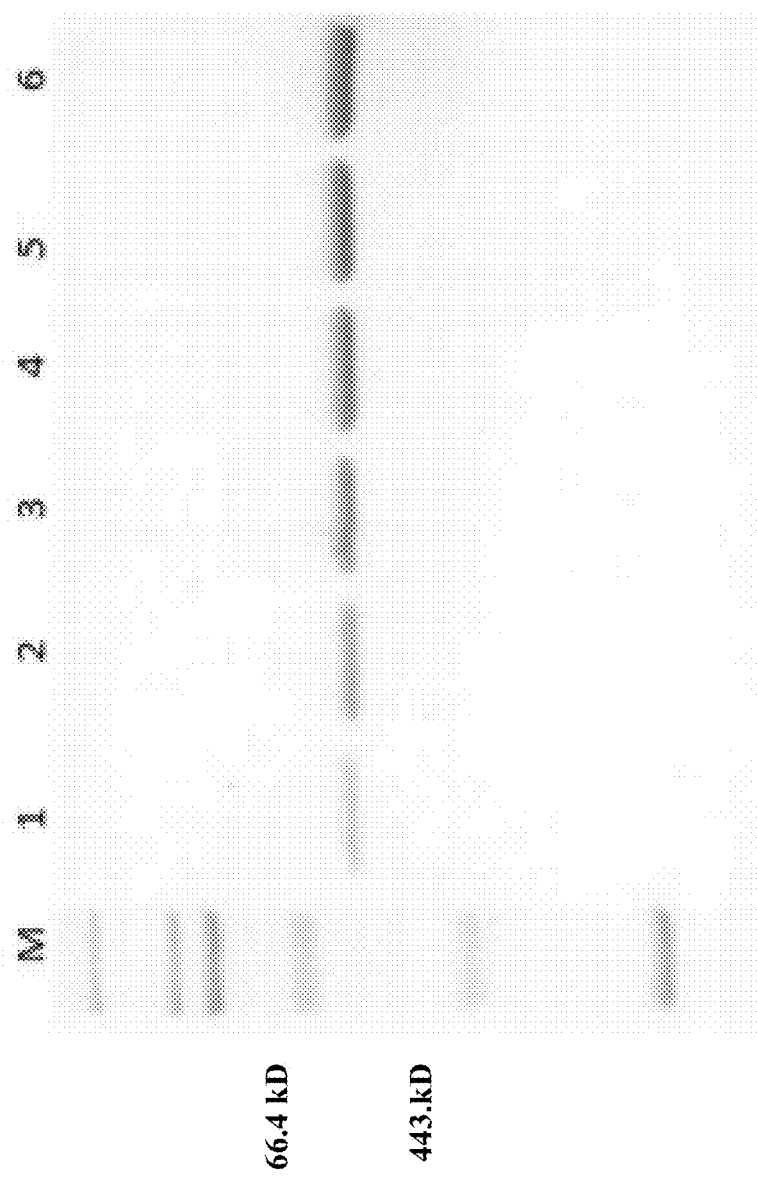
FIG. 6 shows the SDS-PAGE results of the HPV58 L1 proteins having 5, 15, 27, 40, 60 or 70 amino acids truncated at the N-terminal, respectively, i.e. HPV58N5C-L1, HPV58N15C-L1, HPV58N27C-L1, HPV58N40C-L1, HPV58N60C-L1, HPV58N70C-L1 (their amino acid sequences were set forth in SEQ ID NOS:2, 3, 4, 5, 6 and 7, respectively), as obtained in Example 6. Lane M: protein molecular weight marker; Lane 1: the truncated HPV58 L1 protein HPV58N5C-L1 (the loading volume was 10 μL); Lane 2: the truncated HPV58 L1 protein HPV58N15C-L1 (the loading volume was 10 μL); Lane 3: the truncated HPV58 L1 protein HPV58N27C-L1 (the loading volume was 10 μL); Lane 4: the truncated HPV58 L1 protein HPV58N40C-L1 (the loading volume was 10 μL); Lane 5: the truncated HPV58 L1 protein HPV58N60C-L1 (the loading volume was 10 μL); Lane 6: the truncated HPV58 L1 protein HPV58N70C-L1 (the loading volume was 10 μL). The results show that the HPV58 L1 proteins having 5, 15, 27, 40, 60 or 70 amino acids truncated at the N-terminal, respectively, i.e. HPV58N5C-L1, HPV58N15C-L1, HPV58N27C-L1, HPV58N40C-L1, HPV58N60C-L1, HPV58N70C-L1, as obtained in Example 6, reached a purity above 98%.
Figure 7A:
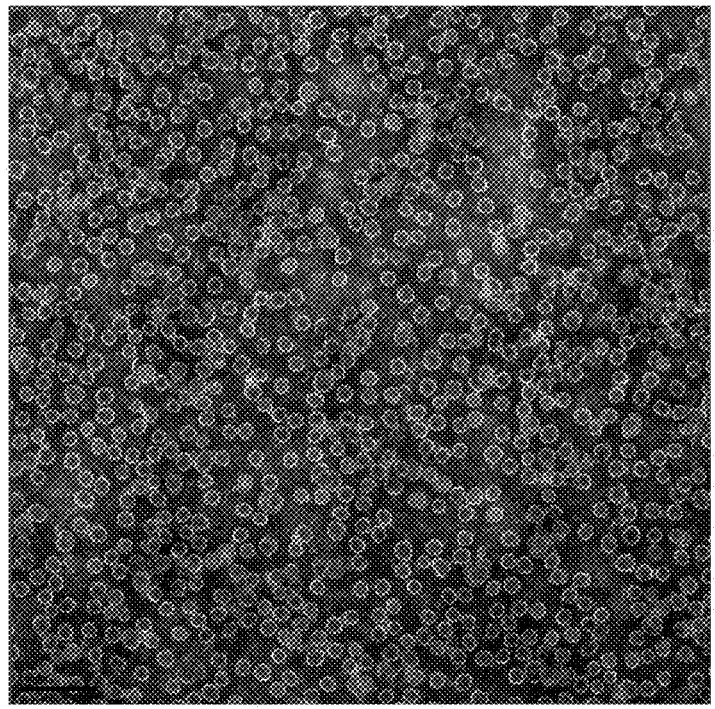
FIGS. 7A-F show the transmission electron microscopy (TEM) photographs of HPV58N5C-L1, HPV58N15C-L1, HPV58N27C-L1, HPV58N40C-L1, HPV58N60C-L1, and HPV58N70C-L1 VLPs obtained in Example 6 (taken at 50,000× magnification, Bar=0.2 μm).
Figure 7B:
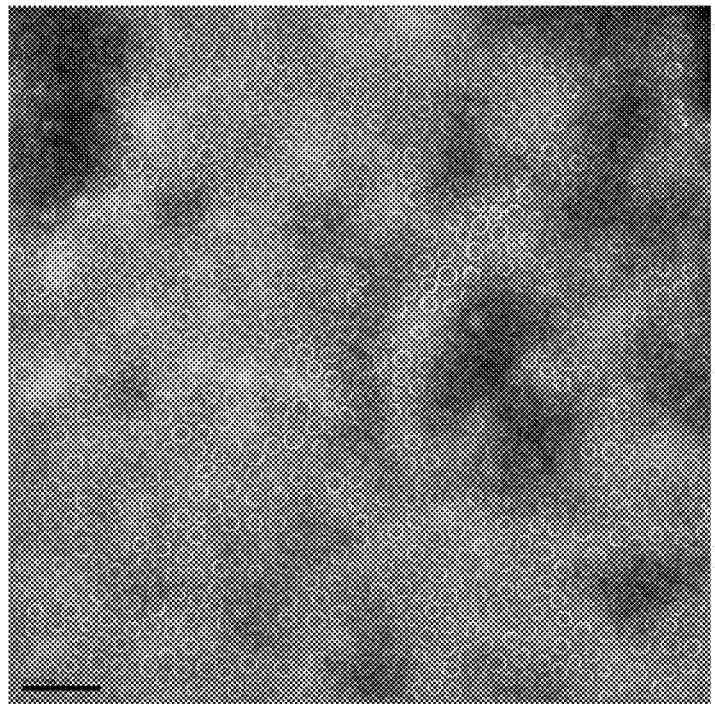
Figure 7C:
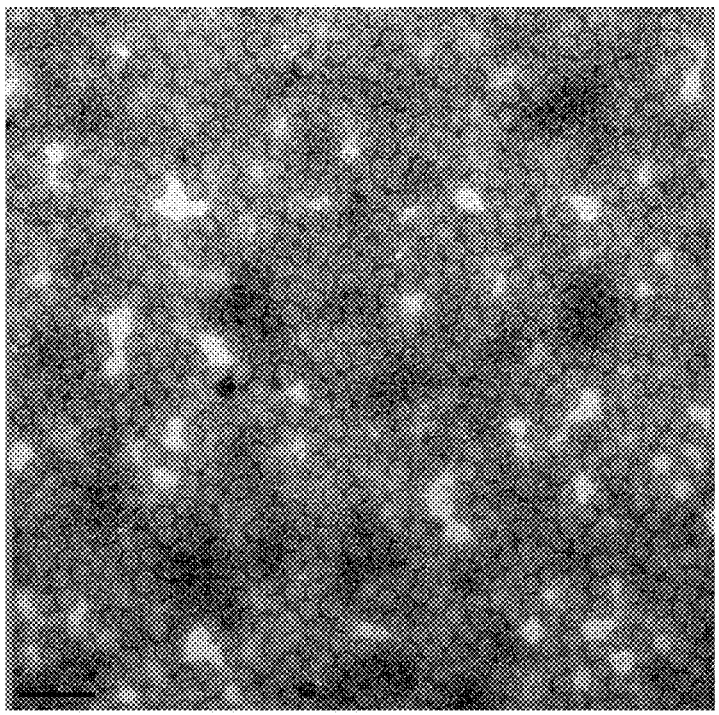
Figure 7D:
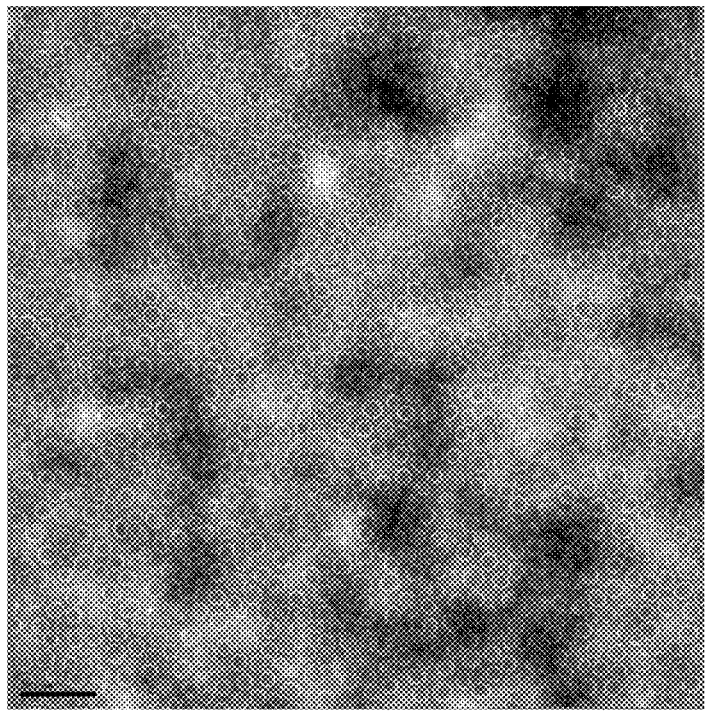
Figure 7E:
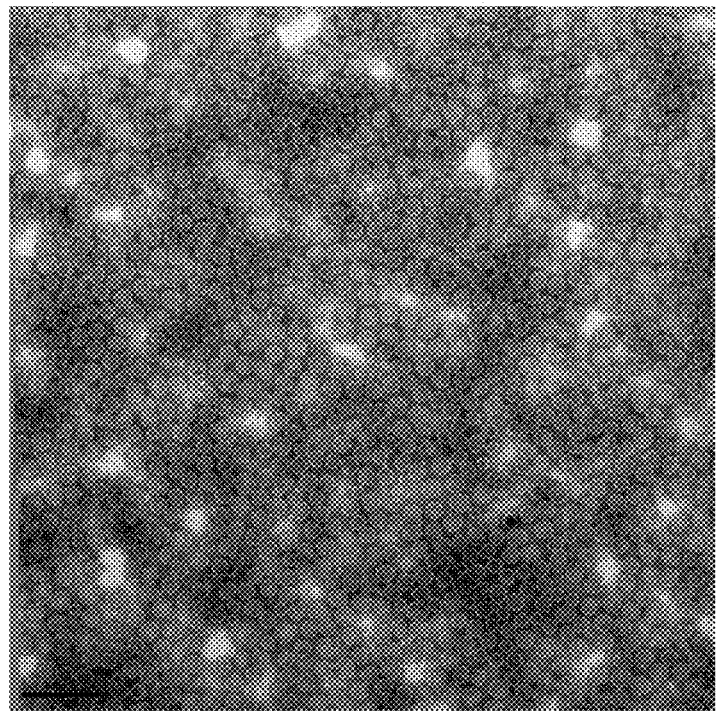
Figure 7F:
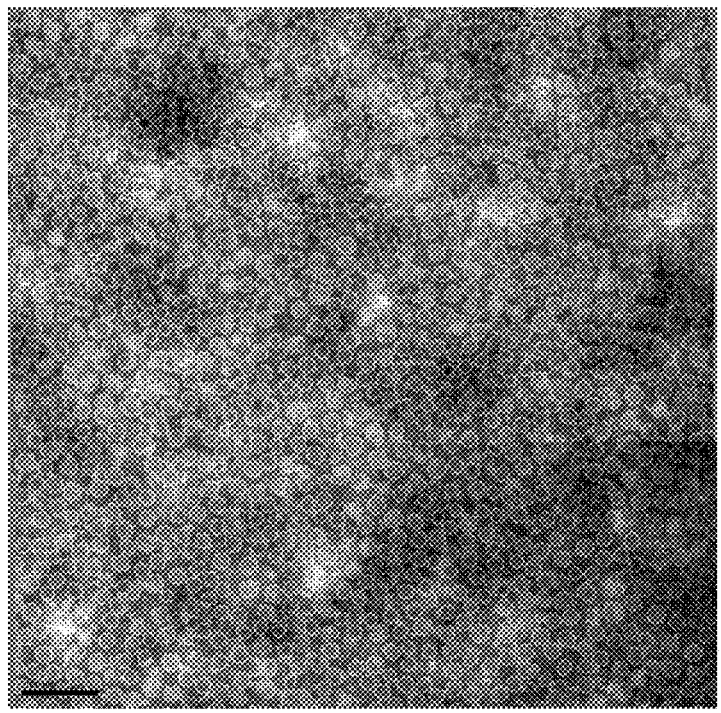
Figure 8A:
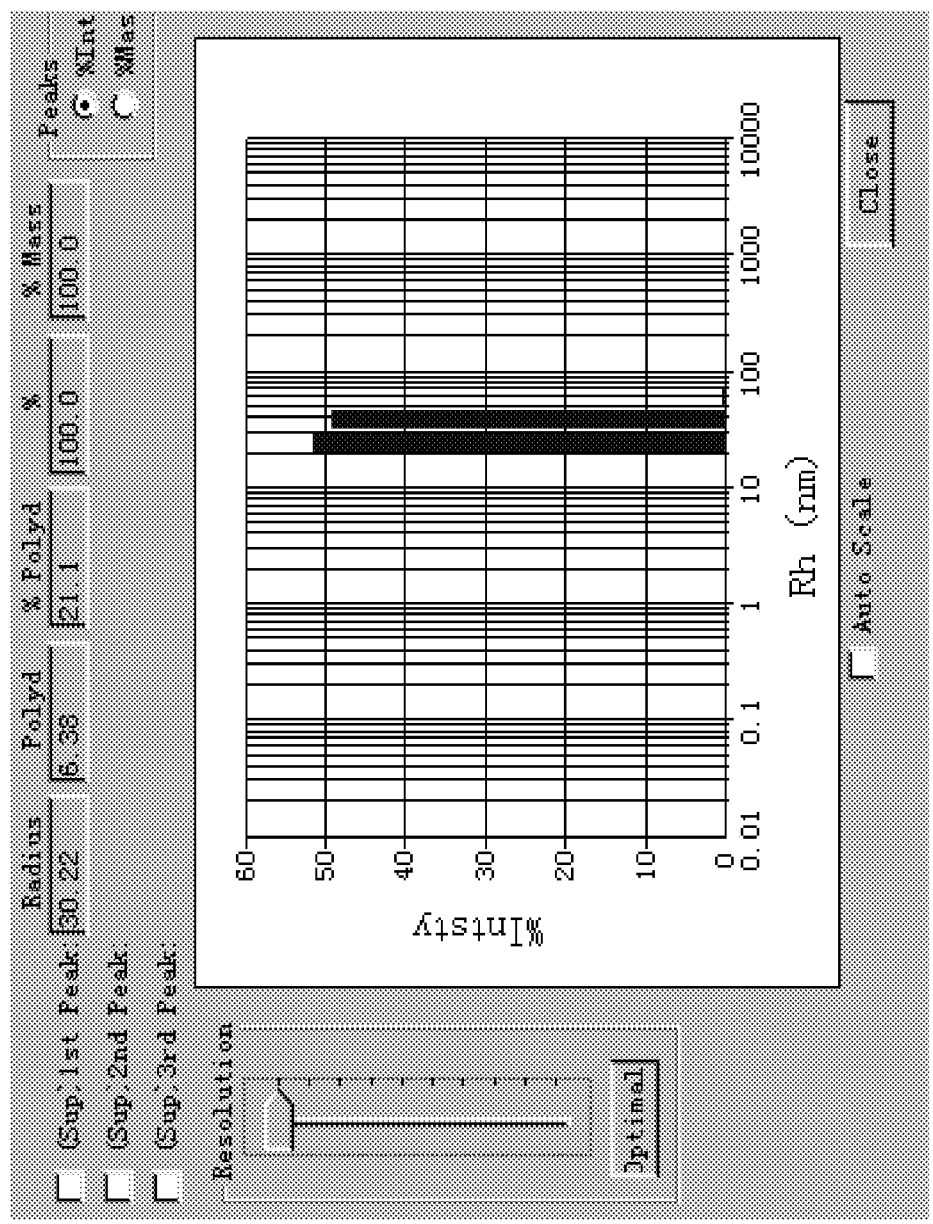
FIGS. 8A-F show the dynamic light-scattering measurement results of HPV58N5C-L1, HPV58N15C-L1, HPV58N27C-L1, HPV58N40C-L1, HPV58N60C-L1, and HPV58N70C-L1 VLPs obtained in Example 6.
Figure 8B:
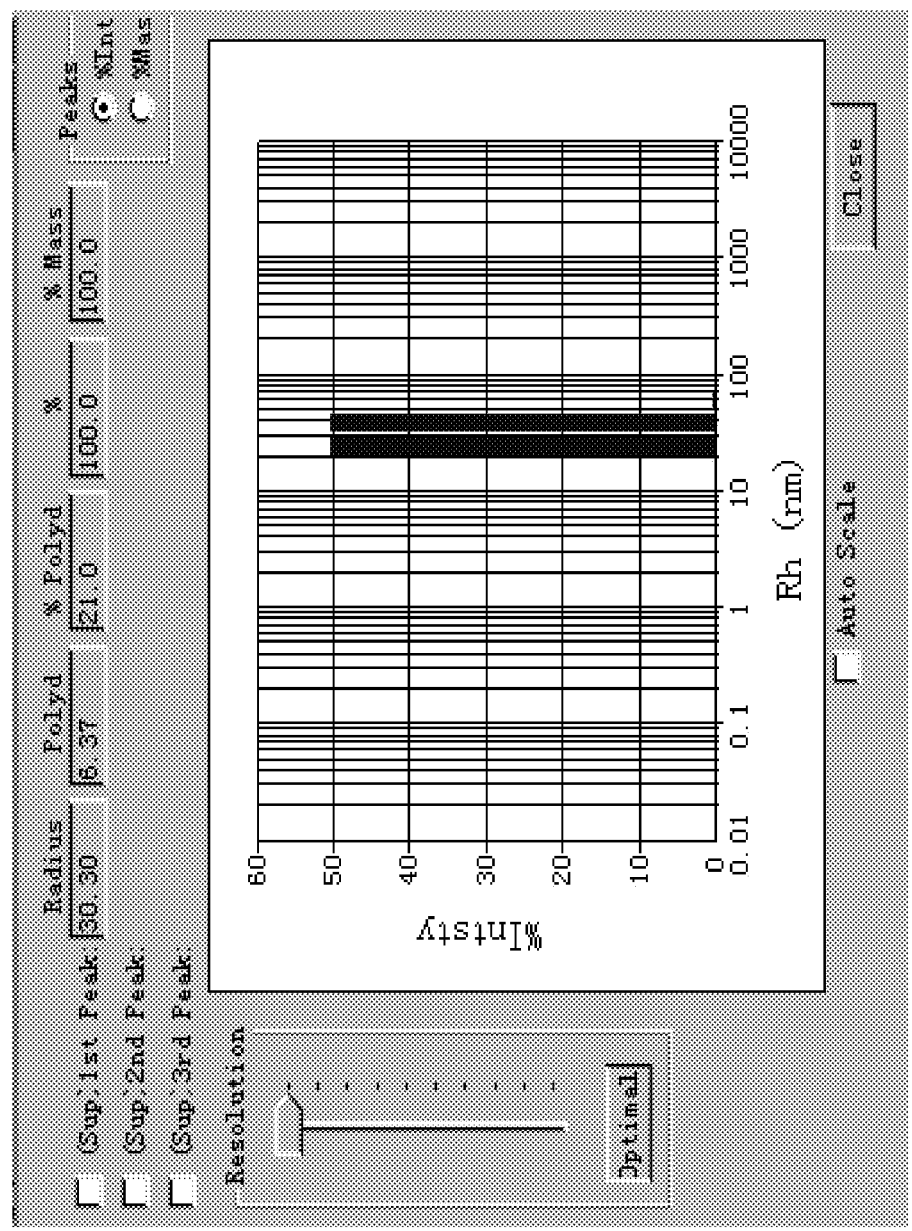
Figure 8C:
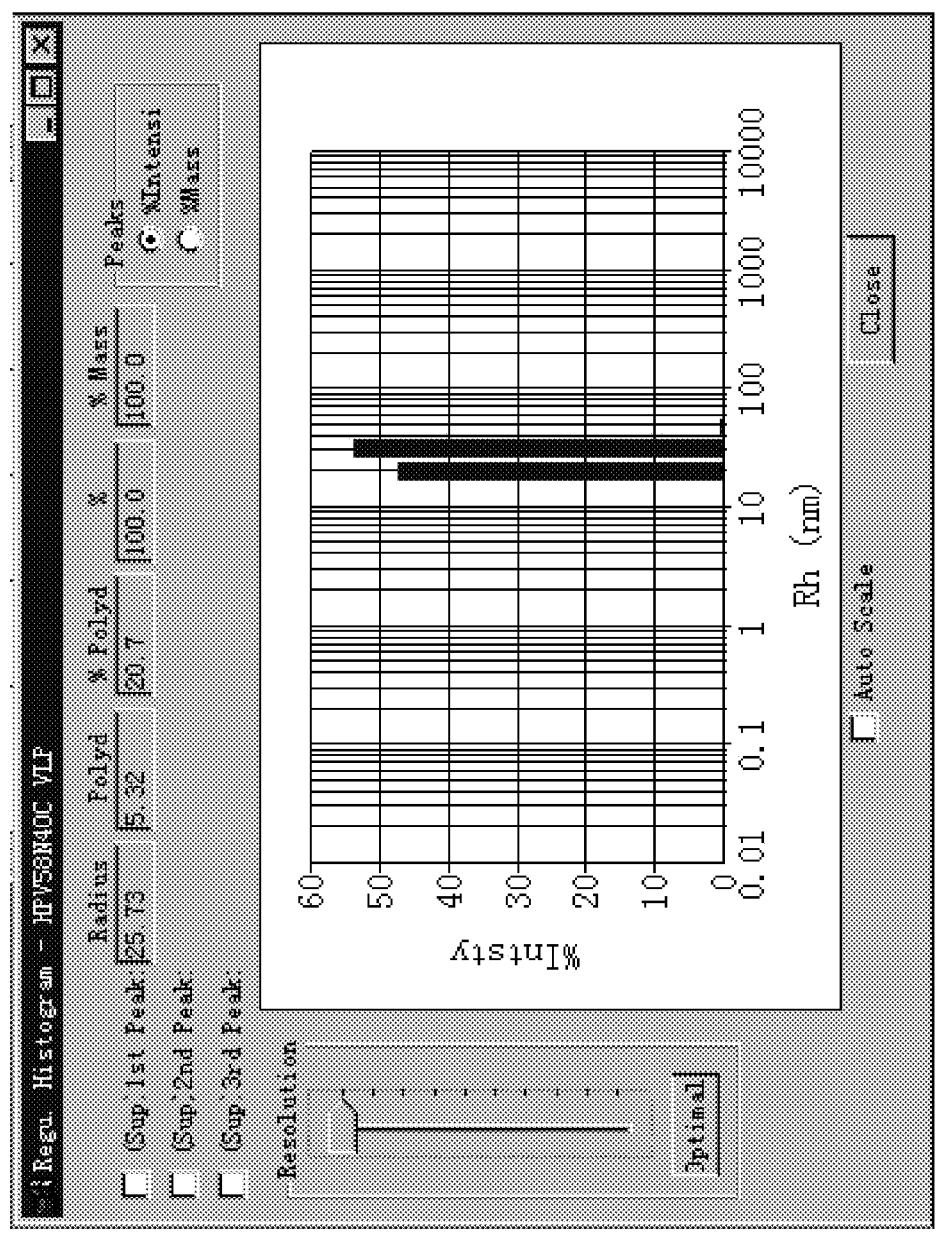
Figure 8D:
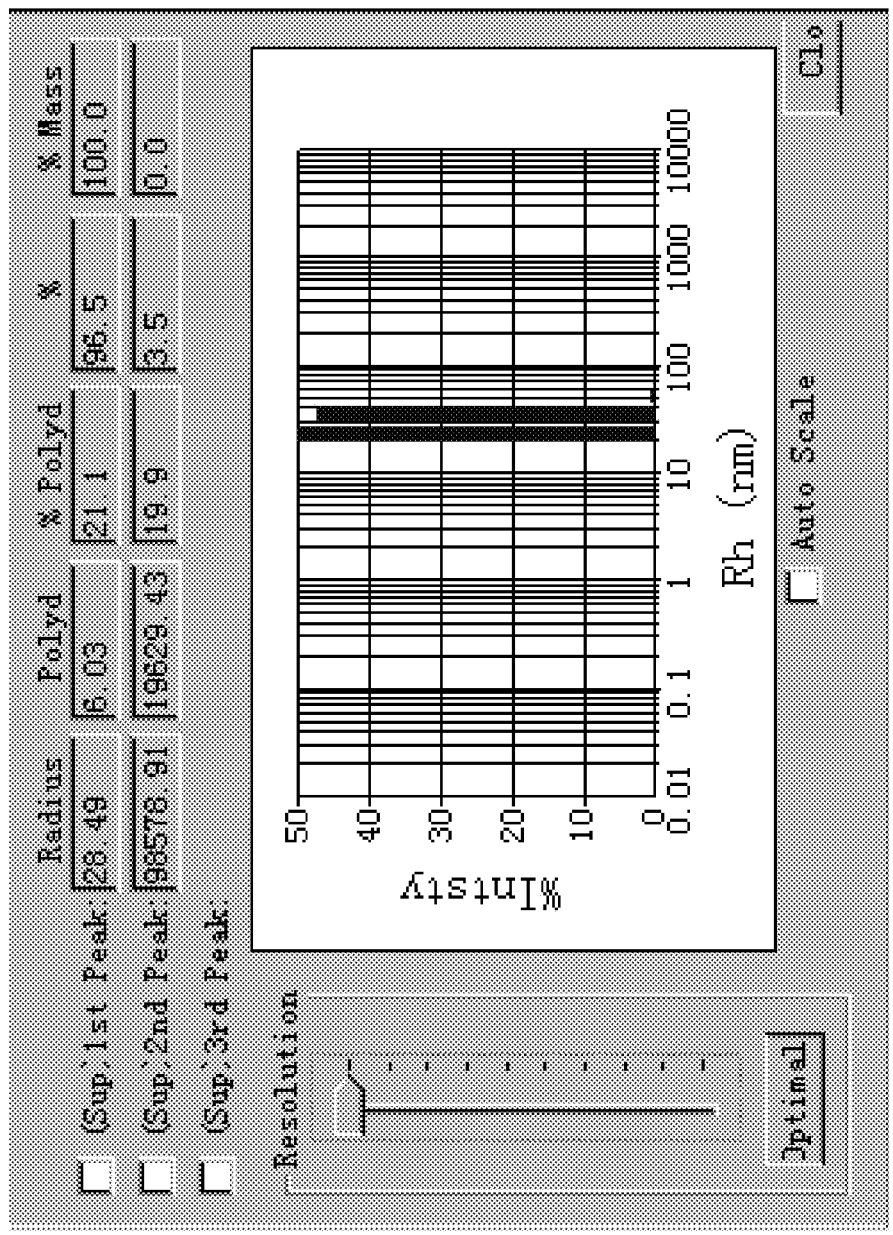
Figure 8E:
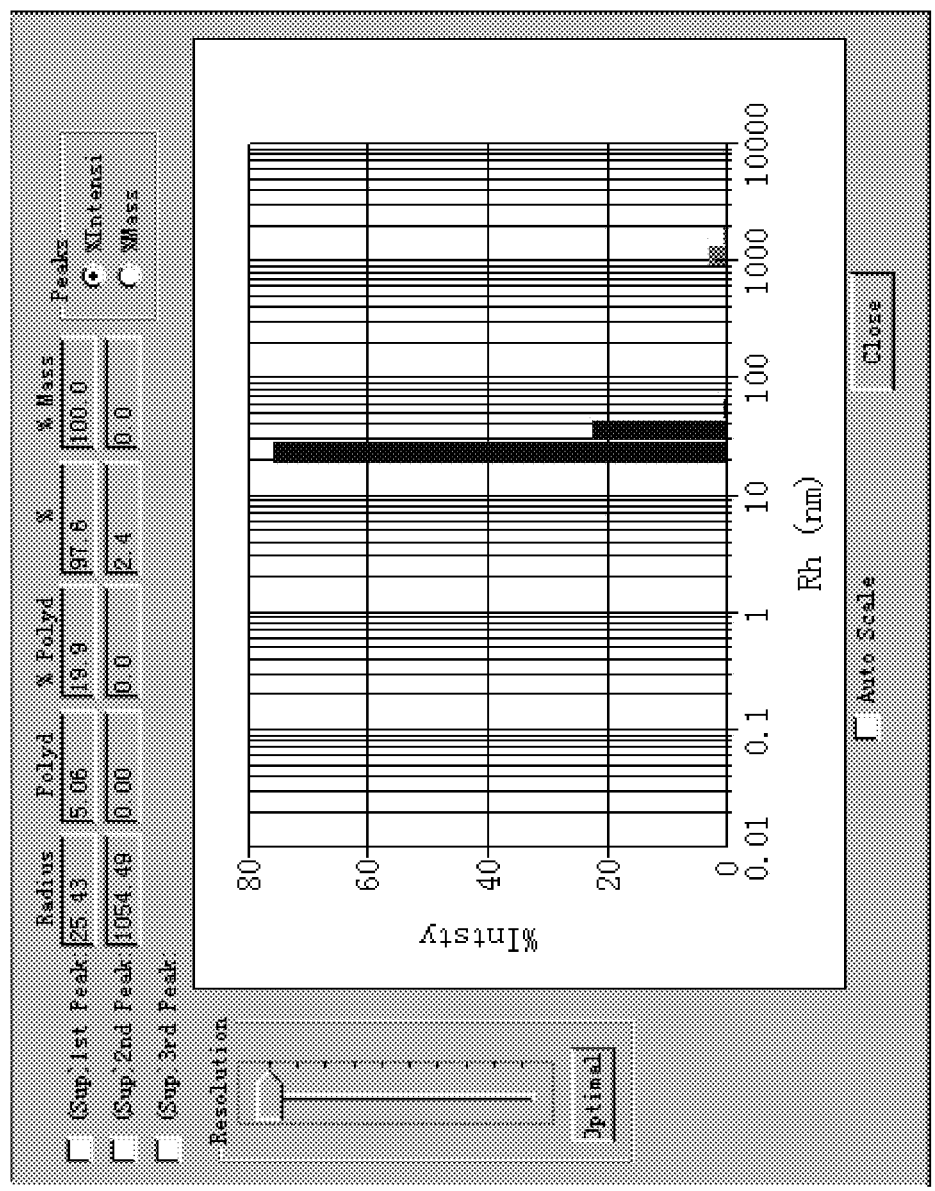
Figure 8F:
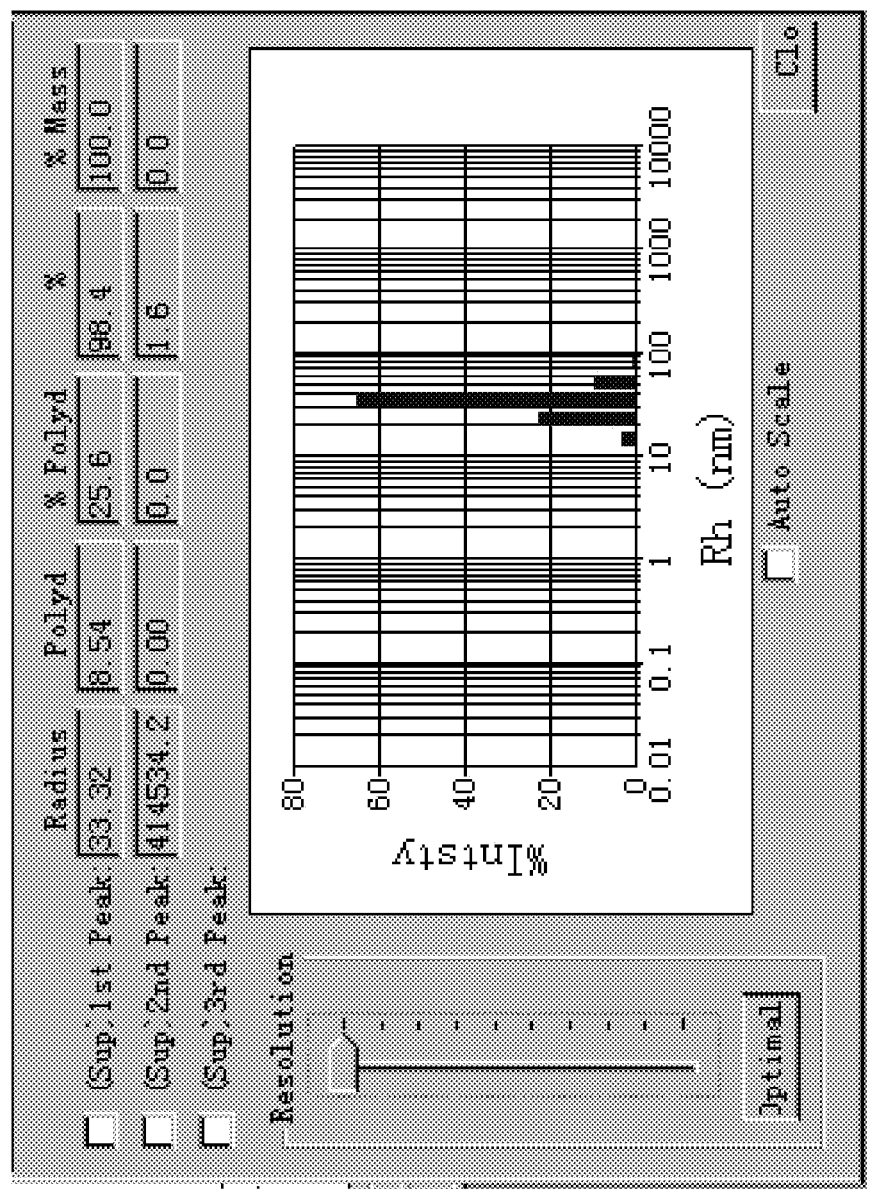

Example 6: Preparation and Morphologic Observation of Other Truncated Proteins and VLPs HPV58 L1 proteins having 5, 15, 27, 40, 60 or 70 amino acids truncated at the N-terminal, respectively, i.e. HPV58N5C-L1, HPV58N15C-L1, HPV58N27C-L1, HPV58N40C-L1, HPV58N60C-L1, HPV58N70C-L1 (their amino acid sequences were set forth in SEQ ID NOS:2, 3, 4, 5, 6 and 7, respectively; their DNA sequences were set forth in SEQ ID NOS:10, 11, 12, 13, 14 and 15, respectively), were prepared and purified basically by the methods as described in Examples 1-3. The proteins thus obtained had a purity of above 98% (see FIG. 6).

The purified HPV58N5C-L1, HPV58N15C-L1, HPV58N27C-L1, HPV58N40C-L1, HPV58N60C-L1, and HPV58N70C-L1 proteins were assembled into VLPs basically by the method as described in Example 4, respectively, designated as HPV58N5C-L1 VLPs, HPV58N15C-L1 VLPs, HPV58N27C-L1 VLPs, HPV58N40C-L1 VLPs, HPV58N60C-L1 VLPs, and HPV58N70C-L1 VLPs, respectively.

HPV58N5C-L1 VLPs, HPV58N15C-L1 VLPs, HPV58N27C-L1 VLPs, HPV58N40C-L1 VLPs, HPV58N60C-L1 VLPs, and HPV58N70C-L1 VLPs were subjected to transmission electron microscopy and dynamic light scattering observation basically by the method as described in Example 5, respectively. The results were shown in FIG. 7 and FIG. 8. FIG. 7 showed that the truncated proteins could form a large number of VLPs with a radius of about 25 nm, wherein the particle size was consistent with the theoretic size and the particles were homogenous. FIG. 8 showed that HPV58N5C-L1, HPV58N15C-L1, HPV58N27C-L1, HPV58N40C-L1, HPV58N60C-L1, and HPV58N70C-L1 VLPs had a hydrodynamic radius of about 25 nm and a particle assembly rate of 100%.

In addition, it was demonstrated by the method as described in Example 5 that the HPV58N5C-L1, HPV58N15C-L1, HPV58N27C-L1, HPV58N40C-L1, HPV58N60C-L1, and HPV58N70C-L1 VLPs obtained in the invention also had good immunogenicity, could induce the generalization of neutralization antibodies with a high titer in animals, and therefore could be used as an effective vaccine for the prevention of HPV infection.

Although the specific embodiments of the present invention have been described in details, those skilled in the art would understand that, according to the teachings disclosed in the specification, various modifications and changes can be made without departing from the sprit or scope of the present invention as generally described, and that such modifications and changes are within the scope of the present invention. The scope of the present invention is given by the appended claims and any equivalents thereof.

The invention claimed is:

1. A truncated HPV58 L1 protein, wherein said truncated HPV58 L1 protein has the amino acid sequence as set forth in SEQ ID NO: 1.

2. An isolated nucleic acid, encoding the truncated HPV58 L1 protein according to claim 1.

3. A vector comprising the isolated nucleic acid according to claim 2.

4. A host cell, wherein said host cell comprises the isolated nucleic acid according to claim 2 or a vector comprising the isolated nucleic acid.

5. A HPV58 virus-like particle, comprising or consisting of the truncated HPV58 L1 protein according to claim 1.

6. A pharmaceutical composition or vaccine comprising the HPV58 virus-like particle according to claim 5, and optionally comprising pharmaceutically acceptable carriers and/or excipients.

7. The pharmaceutical composition or vaccine according to claim 6, wherein the HPV58 virus-like particle is present at an amount effective for preventing HPV infection or cervical cancer.

8. A method of preventing HPV infection or a disease caused by HPV infection comprising administering the HPV58 virus-like particle according to claim 5.

9. The method according to claim 8, wherein HPV infection is HPV58 infection.

10. The method according to claim 9, wherein the disease caused by HPV infection is cervical cancer.

* * * * *